(12) United States Patent
Kelley et al.

(10) Patent No.: US 9,217,179 B2
(45) Date of Patent: Dec. 22, 2015

(54) SYSTEMS AND METHODS FOR MULTIPLEXED ELECTROCHEMICAL DETECTION

(71) Applicant: The Governing Council of the University of Toronto, Toronto, Ontario (CA)

(72) Inventors: Shana O. Kelley, Toronto (CA); Edward H. Sargent, Toronto (CA); Brian Lam, Toronto (CA)

(73) Assignee: The Governing Council of the University of Toronto, Toronto, Ontario (CA)

( * ) Notice: Subject to any disclaimer, the term of this patent is extended or adjusted under 35 U.S.C. 154(b) by 10 days.

(21) Appl. No.: 13/843,323

(22) Filed: Mar. 15, 2013

(65) Prior Publication Data

US 2013/0316340 A1    Nov. 28, 2013

Related U.S. Application Data

(60) Provisional application No. 61/651,132, filed on May 24, 2012.

(51) Int. Cl.

| | |
|---|---|
| *C12M 1/00* | (2006.01) |
| *C12M 1/34* | (2006.01) |
| *C12M 3/00* | (2006.01) |
| *G01N 15/06* | (2006.01) |
| *G01N 33/48* | (2006.01) |
| *G01N 27/00* | (2006.01) |
| *G01N 27/26* | (2006.01) |
| *C12Q 1/68* | (2006.01) |
| *C12Q 1/00* | (2006.01) |
| *G01N 33/543* | (2006.01) |

(52) U.S. Cl.
CPC .............. *C12Q 1/6876* (2013.01); *C12Q 1/001* (2013.01); *C12Q 1/6825* (2013.01); *G01N 33/5438* (2013.01)

(58) Field of Classification Search
USPC ......... 435/6.1, 283.1, 288.4; 422/68.1, 82.01; 204/400, 406, 411
See application file for complete search history.

(56) References Cited

U.S. PATENT DOCUMENTS

| | | | |
|---|---|---|---|
| 5,264,103 A | 11/1993 | Yoshioka et al. | |
| 5,296,125 A | 3/1994 | Glass et al. | |
| 5,545,531 A | 8/1996 | Rava et al. | |
| 6,045,676 A | 4/2000 | Mathies et al. | |
| 6,331,441 B1 | 12/2001 | Balch et al. | |
| 6,361,671 B1 | 3/2002 | Mathies et al. | |
| 6,673,533 B1 | 1/2004 | Wohlstadter et al. | |
| 7,172,897 B2 | 2/2007 | Blackburn et al. | |
| 7,341,834 B2 | 3/2008 | Yang | |
| 7,361,470 B2 | 4/2008 | Kelley et al. | |
| 7,741,033 B2 | 6/2010 | Kelley et al. | |
| 7,972,494 B2 | 7/2011 | Tam | |
| 8,197,775 B2 | 6/2012 | Johnston et al. | |
| 8,313,895 B2 | 11/2012 | Pollack et al. | |
| 2002/0090649 A1 | 7/2002 | Chan et al. | |
| 2002/0123048 A1 | 9/2002 | Gau | |
| 2004/0022677 A1 | 2/2004 | Wohlstadter et al. | |
| 2008/0210573 A1 | 9/2008 | Yang | |
| 2009/0242429 A1 | 10/2009 | Sitdikov et al. | |
| 2011/0233075 A1 | 9/2011 | Soleymani et al. | |

OTHER PUBLICATIONS

International Search Report and Written Opinion dated May 31, 2013 in International Application No. PCT/US2013/032655 (12 pages).

Soleymani et al. "Programming the Detection Limits of Biosensors through Controlled Nanostructuring" Nature Nanotechnology DOI: 10.1038/NNANO2009.276; Published Online Sep. 27, 2009, (5 pages).

Alligrant et al. "Electrochemical Detection of Individual DNA Hybridization Events", Lab on a Chip, RSC Publishing; DOI: 10.1039/c2lc40993c, The Royal Society of Chemistry 2012 (6 pages).

Sorgenfrei et al. Label-Free Single-Molecule Detection of DNA-Hybridization Kinetics with a Carbon Nanotube Field-Effect Transistor, Nature Nanotechnology; Published Jan. 23, 2011, DOI:10.1038/NNAN0.2010.275 (7 pages).

Slinker et al. "Multiplexed DNA-Modified Electrodes", JACS Articles, Published on Web Feb. 4, 2010; Division of Chemistry and Chemical Engineering, California Institute of Technology, Pasadena, California 91125, (6 pages).

Xiao, et al. Single-Step Electronic Detection of Femtomolar DNA by Target-Induced Strand Displacement in an Electrode-Bound Duplex, Department of Physics, Materials Department, Institute for Plymers and Organic Solds, and Department of Biochemistry and Program in BioMolecular Science and Engineering, University of California, Santa Barbara, CA 93106; dated Nov. 7, 2006, vol. 103, No. 45, pp. 16677-16680 (4 pages).

Patolsky et al., "Detection of Single-Base DNA Mutations by Enzyme-Amplified Electronic Transduction", 2001 Nature Publishing Group http://biotech.nature.com, Mar. 2001, vol. 19, Institute of Chemistry, The Hebrew University of Jerusalem, Jerusalem 91904, Israel, pp. 253-257.

(Continued)

*Primary Examiner* — Narayan Bhat

(74) *Attorney, Agent, or Firm* — Ropes & Gray LLP

(57) ABSTRACT

Contemplated methods and devices comprise performing electrochemical sample analysis in a multiplexed electrochemical detector having reduced electrical cross-talk. The electrochemical detector includes electrodes that share a common lead from a plurality of leads. The sample, which may be a liquid sample, is introduced into one or more sample wells and a signal is applied to at least one of the electrodes. A response signal is measured while simultaneously applying a substantially fixed potential to each of a remainder of the plurality of leads.

22 Claims, 18 Drawing Sheets

(56) References Cited

OTHER PUBLICATIONS

Pheeney et al. "DNA Sensing by Electrocatalysis with Hemoglobin" Division of Chemistry and Chemical Engineering, California Institute of Technology, Pasadena CA 91125, Edited by Royce W. Murray, University of North Carolina at Chapel Hill, Chapel Hill, NC, and approved May 22, 2012 (received fro review Mar. 23, 2012), pp. 11528-11533/PNAS/Jul. 17, 2012, vol. 109, No. 29 (www.pnas.org/lookup/suppl/doi:10.1073/pnas.1201551109/-/DCSupplemental).

Wanunu et al. "Rapid Electronic Detection of Probe-Specific MicroRNAs Using Thin Nanopore Sensors," Nature Nanotechnology, Published Online: Oct. 24, 2010/DOI:10.1038/NNANO2010.202, vol. 5/Nov. 2010/ www.nature.com/naturenanotechnology, 2010 Macmillan Publishers Limited, pp. 807-814.

Khan et al. "In Situ, Label-Free DNA Detection Using Organic Transistor Sensors," Advanced Materials, www.advmat.de, Materials Views, www.MaterialsViews.com; Adv. Mater. 2010, 22, pp. 4452,4456.

Das et al. "Protein Detection Using Arrayed Microsensor Chips: Tuning Sensor Footprint to Achieve Ultrasensitive Readout of CA-125 in Serum and Whole Blood," pubs.acs.org/ac, ACS Publications, dxdoi.org/10.102/ac102917f/Anal.Chem. 2011, 83, pp. 1167-1172.

Duan et al. "Quantification of the Affinities and Kinetics of Protein Interactions Using Silicon Nanowire Biosensors," Nature Nanotechnology, Published Online: May 27, 2012, DOI:10.1038/NNANO.2012.82, vol. 7, Jun. 2002, www.nature.com/naturenanotechnology pp. 401-407.

Tang et al "Ultrasensitive Electrochemical Immunosensor for Clinical Immunoassay Using Thionine-Doped Magnetic Gold Nanosphers as Lables and Horseradish Peroxidase as Enhancer," Anal. Chem, vol. 80, Mar. 1, 2008, pp. 1582-1588.

Malhotra et al. "Ultrasensitive Electrochemical Immunosensor for Oral Cancer Biomarker IL-6 Using Carbon Non0tube Forest Electrodes and Multilabel Amplification," Analytical Chemistry, vol. 82, No. 8, Apr. 15, 2010 (8 pages).

Xiang, et al. "Ultrasensitive Label-Free Aptamer-Based Electronic Detection," DOI:10.1002/anie.200703242. Angew. Chem. Int. Ed. 2007, 46, pp. 9054-9056.

Das et al. "An Ultrasensitive Universal Detector Based on Neutralizer Displacement," Published Online: Jun. 3, 2012, DOI: 10.1038/NCHEM.1367, Nature Chemistry; vol. 4, Aug. 2012, www.nature.com/naturechemistry; 19 pages.

Zuo et al. "High Specificity, Electrochemical Sandwich Assays Based on Single Aptamer Sequences and Suitable for the Direct Detection of Small-Molecule Targets in Blood and Other Complex Matrices," JACS Communications; Published on Web, May 6, 2009; J. AM. Chem. Soc. 2009, 131, pp. 6944-6945.

Liu et al. "Aptamer-Based Origami Paper Analytical Device for Electrochemical Detection of Adenosine", DOI: 10:10.1002/anie.201202929, Angew. Chem. Int. Ed. 2012, 51, 6925-6928 (4 pages).

Kuang et al. "Biomimetic Chemosensor: Designing Peptide Recognition Elements for Surface Functionalization of Carbon Nanotube Field Effect Transistors" ACSNano, vol. 4, No. 1, 7 pages, 452-458.

Vasilyeva et al. "Direct Genetic Analysis of Ten Cancer Cells: Tuning Sensor Structure and Molecular Probe Design for Efficient mRNA Capture", DOI:10.1002/anie.201006793, Angew. Chem. Int. Ed. 2011, 50, 4137-4141.

Swensen et al. "Continuous, Real-time Monitoring of Cocaine in Undiluted Blood Serum via a Microfluidic, Electrochemical Aptamer-Based Sensor" J/A/C/S Articles, Published on Web Mar. 9, 2009, J. AM Chem. Soc. 2009, 131, 7 pages, 4262-4266.

Lam et al. "Polymerase Chain Reaction-Free, Sample-to-Answer Bacterial Detection in 30 minutes with Integrated Cell Lysis", Analytical Chemistry, ACS Publications, dxdoi.org/10.1021/ac2025996, Anal. Chem. 2012, 84, 21-25, 5 pages.

Mani et al. "Ultrasensitive Immunosensor for Cancer Biomarker Proteins Using Gold Nanoparticle Film Electrodes and Multienzyme-Particle Amplification", vol. 3, No. 3, pp. 584-594, 2009.

Lerner "Hybrids of a Genetically Engineered Antibody and a Carbon Nanotube Transistor for Detection of Prostate Cancer Biomarkers", vol. 6, No. 6, 5143-5149, 10 pages.

Mannoor "Electrical Detection of Pathogenic Bacteria via Immobilized Antimicrobial Peptides", www.pnas.org/cgi/doi/10.1073/pnas.1008768107PNAS Early Edition, 6 pages.

| Array Size | Contacts for Serially-Connected Chip | Contacts for Channel-Based Chip (2 Electrode) | Contacts for Channel-Based Chip (3 Electrode) |
|---|---|---|---|
| 10x10 | 100 | 20 | 30 |
| 20x20 | 400 | 40 | 60 |
| 30x30 | 900 | 60 | 90 |
| 40x40 | 1600 | 80 | 120 |
| 80x80 | 6400 | 160 | 240 |

FIG. 6

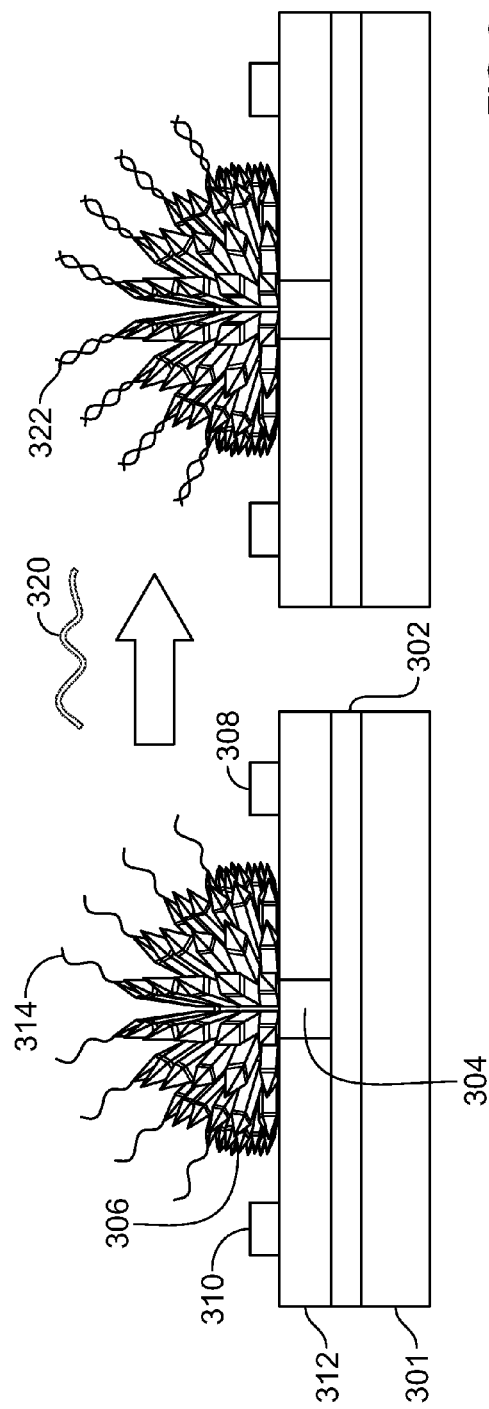
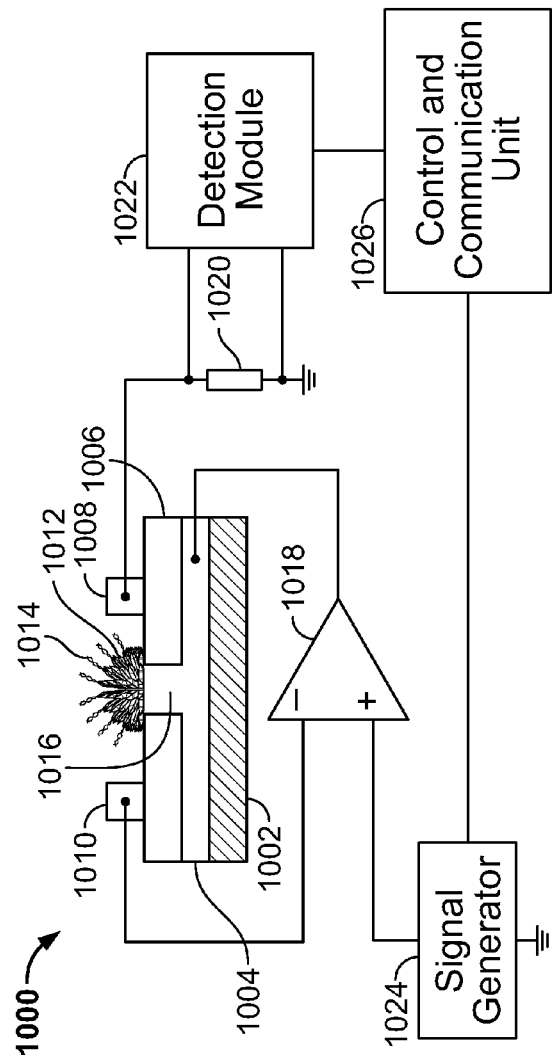

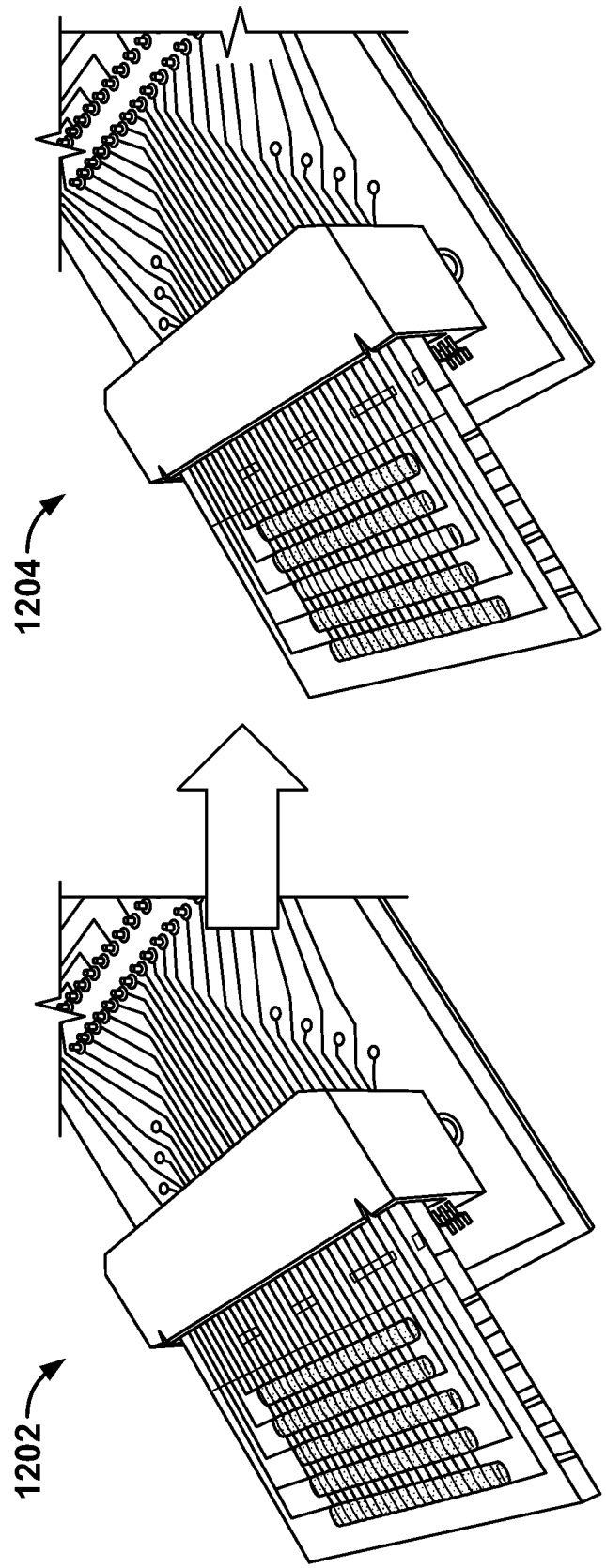

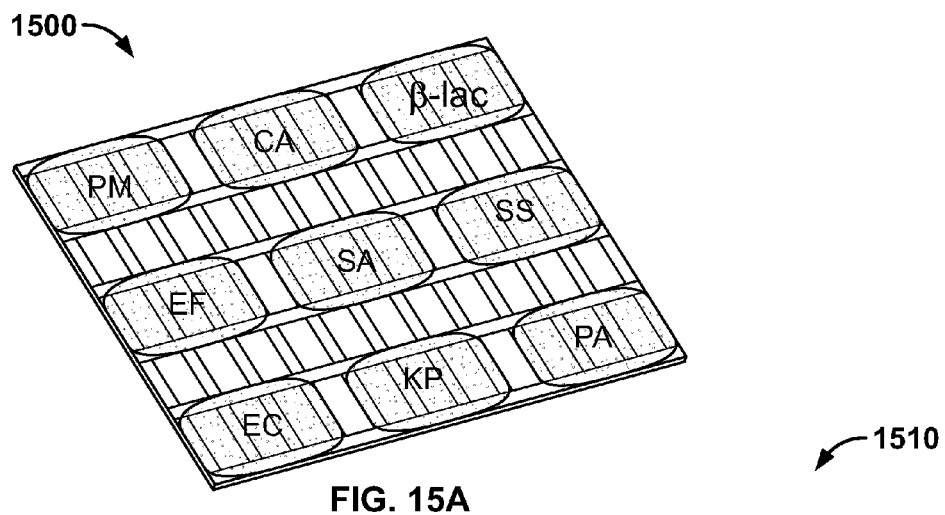
FIG. 15A
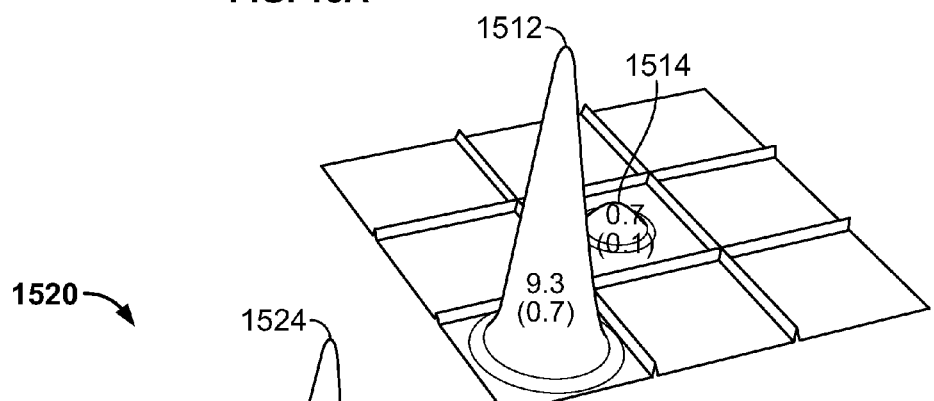
E. coli (- β-lac)  FIG. 15B
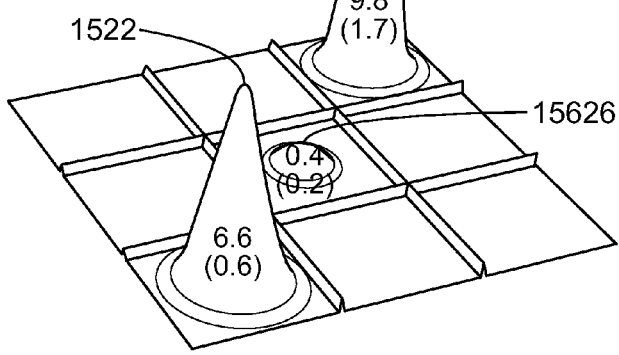
E. coli (+ β-lac)  FIG. 15C S. aureus E. coli (+ β-lac) + S. aureus

SYSTEMS AND METHODS FOR MULTIPLEXED ELECTROCHEMICAL DETECTION

CROSS-REFERENCE TO RELATED APPLICATION

This application claims the benefit of U.S. Provisional Patent Application No. 61/651,132, filed May 24, 2012, which is hereby incorporated by reference herein in its entirety.

SEQUENCE LISTING

The instant application contains a Sequence Listing which has been submitted in ASCII format via EFS-Web and is hereby incorporated by reference herein in its entirety. Said ASCII copy, created on Jun. 20, 2013, is named 109904-0008-101_SL.txt and is 4,822 bytes in size.

TECHNICAL FIELD

The disclosure relates generally to electrochemical detection including, without limitation, systems and methods for analyzing of a wide range of analytes such as nucleic acids, proteins, and small molecules, using a multiplexed electrochemical detector.

BACKGROUND

Testing for diseases, such as infectious disease speciation and antibiotic resistance profiling, often requires interrogating samples for many dozens of biomarkers. Electronic read-out from such large arrays of biosensors has been hampered by the difficulty in generating and addressing large arrays of electrode-based sensors on inexpensive, passive chips. Arrays of biosensors can be generated to work in conjunction with electrochemical reporter systems, enabling multiplexing and detection of analytes in a single chip. Doing so, however, often results in an assay that includes tens, hundreds, or even thousands of electrodes. This large number of electrodes poses a problem for minimizing chip sizes (and hence, manufacturing costs and portability) if each electrode must be coupled to an external contact in order to be independently addressable.

While it is possible to reduce the number of external electrical contacts by sharing such contacts among multiple electrodes through multiplexing, known approaches for doing so pose additional problems. For example, the need for independently-addressed electrical contacts corresponding to each sensor, as well as reference and counter electrodes, requires that highly multiplexed arrays employ an active multiplexing strategy. The additional complexity of integrated active electronics has effectively limited current multiplexed detection systems to a small set of contacts (and hence, low levels of multiplexing) that rely on passive switching mechanisms. Moreover, the design of such chips often leads to substantial electrical cross-talk, which can reduce the overall sensitivity and specificity of detection.

There is therefore a need for improved electrochemical detection systems, devices, and mechanisms.

SUMMARY

Disclosed herein are systems, devices, and methods for providing electrochemical detection of target biomarkers using multiplexed sample analysis. The multiplexed sample analysis includes controlling a signal to one or more electrodes in one or more sample wells, where at least some of the electrodes share a lead or electrical connection. The sample wells can be configured as isolated columns of connected biosensors aligned substantially perpendicular to channels containing liquid sample, which can serve to connect the biosensors to counter electrodes. Use of the liquid switching channels advantageously provides a higher level of multiplexing than can be typically attained with a small set of contacts, making highly multiplexed electrochemical sensing feasible on a passive integrated circuit. However, other connectors (besides solution-based switching channels) can be used to couple the counter electrodes to the working electrodes without departing from the scope hereof. The multiplexed sample analysis includes techniques to improve sensitivity of the detection by reducing electrical cross-talk between electrodes sharing the same electrical contact. Electrical cross-talk can be reduced to below measurable levels by selectively applying input signals to one of a plurality of leads while simultaneously applying a substantially fixed potential to each of the remaining leads that are in electrical communication with the selected lead. The substantially fixed potential can be selected so as to reduce current flow from the remaining leads to the counter electrode at which a response signal is being measured, thereby making it possible to detect even small concentrations of the target analyte in the sample.

In one aspect, a method for performing electrochemical analysis comprises introducing a sample into a multiplexed electrochemical detector. The multiplexed electrochemical detector comprises a first sample well and a plurality of leads. The first sample well comprises a first plurality of working electrodes each adapted to be electrically coupled to one of the plurality of leads, and the first plurality of working electrodes are adapted to be electrically coupled to a first counter electrode. A first signal is applied to a first lead of the plurality of leads, and a first response signal is measured from the first counter electrode while simultaneously applying a substantially fixed potential to each of a first remainder of the plurality of leads. The substantially fixed potential can be any suitable potential selected to reduce current flow from the first remainder of the plurality of leads to the first counter electrode. In some implementations, the substantially fixed potential corresponds to a ground potential. It is determined whether a first target analyte is present in the sample based on the first response signal. In some implementations, the multiplexed electrochemical detector further comprises a second sample well. The second sample well comprises a second plurality of working electrodes each adapted to be electrically coupled to one of the first plurality of working electrodes via one of the plurality of leads. Each of the second plurality of working electrodes is adapted to be electrically coupled to a second counter electrode. A second signal is applied to a second lead of the plurality of leads, and a second response signal is measured from the second counter electrode while simultaneously applying a substantially fixed potential to each of a second remainder of the plurality of leads. It is determined whether a second target analyte is present in the sample based on the second response signal.

In some implementations, the plurality of working electrodes are adapted to be electrically coupled to the first counter electrode by a first fluid portion of the sample that simultaneously contacts each of the first plurality of working electrodes and the first counter electrode. The second plurality of working electrodes are adapted to be electrically coupled to the second counter electrode by a second fluid portion of the sample that simultaneously contacts each of the second plurality of working electrodes and the second counter electrode. The second fluid portion is substantially physically isolated from the first fluid portion during the measuring of the first and second response signals. Each of the plurality of leads is arranged in one of a plurality of rows on a solid support, and each of the first and second sample wells is formed from first and second elongated channels, respectively, that run substantially perpendicular to each of the plurality of rows.

In some implementations, each of the first and second channels comprises hydrophobic and hydrophilic regions. The electrochemical detector may also include a first plurality of probes each tethered to one of the first plurality of working electrodes, wherein the first plurality of probes is selected to hybridize with the first target analyte. Additionally, the electrochemical detector may include a second plurality of probes tethered to one of the second plurality of working electrodes, wherein the second plurality of probes is selected to hybridize with the second target analyte but not the first target analyte.

In some implementations, each of the first and second counter electrodes is coupled to a common potentiostat, and wherein measuring the first and second response signals comprises sequentially measuring the first and second response signals using the common potentiostat.

In some implementations, the first counter electrode is coupled to a first potentiostat and second counter electrode is coupled to a second potentiostat, the method further comprising sequentially measuring the first and second response signals using the first and second potentiostats, respectively.

In some implementations, the first and second pluralities of working electrodes comprise one or more nanostructured microelectrodes.

In some implementations, the method comprises applying to the electrochemical detector an electrochemical reagent comprising $Ru(NH_3)_6^{3+}$ and $Fe(CN)_6^{3-}$.

In some implementations, the first and second pluralities of probes are selected from nucleic acids, peptide nucleic acids, locked nucleic acids, proteins, and peptides.

In some implementations, determining whether the first target analyte is present in the sample comprises determining that a magnitude of the first response signal is greater than a threshold value. The method may provide an indicator of whether the first target analyte is present in the sample, the indicator selected from a magnitude of the first response signal, a concentration of the first target analyte determined based on the first response signal, a color-coded indicator selected based on the first response signal, a symbol selected based on the first response signal, a graphical representation of the first response signal over a plurality of values of the first voltage signal, and any suitable combination thereof.

In some implementations, the sample is a liquid sample. The liquid sample may contain bacteria. The bacteria in the sample are lysed prior to introducing the sample into the multiplexed electrochemical detector.

In another aspect, a multiplexed electrochemical detection system comprises a solid support, a plurality of leads affixed to the solid support, and a first sample well within the solid support. The first sample well comprises a first plurality of working electrodes each adapted to be electrically coupled to one of the plurality of leads. The system further comprises a first counter electrode adapted to be electrically coupled to the first plurality of working electrodes. The system also comprises detection circuitry configured to apply a first signal to a first lead of the plurality of leads, and measure a first response signal from the first counter electrode while simultaneously applying a substantially fixed potential to each of a first remainder of the plurality of leads. The first response signal can enable the determination of whether a first target analyte is present in a sample. In some implementations, the system comprises a second sample well within the solid support. The second sample well comprises a second plurality of working electrodes each adapted to be electrically coupled to one of the plurality of leads. The system further comprises a second counter electrode adapted to be electrically coupled to the first plurality of working electrodes. The detection circuitry is further configured to apply a second signal to a second lead of the plurality of leads, and measure a second response signal from the second counter electrode while simultaneously applying a substantially fixed potential to each of a second remainder of the plurality of leads. The second response signal can enable the determination of whether a first target analyte is present in the sample.

In some implementations, the first plurality of working electrodes are adapted to be electrically coupled to the first counter electrode by the presence of a first fluid portion of the sample capable of simultaneously contacting each of the first plurality of working electrodes and the first counter electrode. The second plurality of working electrodes are adapted to be electrically coupled to the second counter electrode by the presence of a second fluid portion of the sample capable of simultaneously contacting each of the second plurality of working electrodes and the second counter electrode. The second fluid portion is substantially physically isolated from the first fluid portion during said measuring of the first and second response signals.

In some implementations, each of the plurality of leads is arranged in one of a plurality of rows on the solid support, and each of the first and second sample wells is formed from first and second elongated channels, respectively, that run perpendicular to each of the plurality of rows. Each of the first and second channels may comprise hydrophobic and hydrophilic regions.

In some implementations, the system comprises a first plurality of probes each tethered to one of the first plurality of working electrodes. The first plurality of probes is selected to hybridize with the first target analyte. The system further comprises a second plurality of probes tethered to one of the second plurality of working electrodes. The second plurality of probes is selected to hybridize with the second target analyte but not the first target analyte.

In some implementations, each of the first and second counter electrodes are adapted to couple to a common potentiostat, and the detection circuitry is further configured to measure the first and second response signals sequentially using the common potentiostat.

In some implementations, the first counter electrode is adapted to couple to a first potentiostat and second counter electrode is adapted to couple to a second potentiostat, and the detection circuitry is further configured to measure the first and second response signals sequentially using the first and second potentiostats, respectively.

In some implementations, the first and second pluralities of working electrodes comprise one or more nanostructured microelectrodes.

In some implementations, an electrochemical reagent comprising $Ru(NH_3)_6^{3+}$ and $Fe(CN)_6^{3-}$ is applied to the electrochemical detector.

In some implementations, the first and second pluralities of probes are selected from nucleic acids, peptide nucleic acids, locked nucleic acids, proteins, and peptides.

In some implementations, the detection circuitry is configured to interface with a processor, the processor being configured to determine that a magnitude of the first response signal is greater than a threshold value. The processor may be further configured to provide an indicator of whether the first target analyte is present in the sample, the indicator selected from a magnitude of the first response signal, a concentration of the first target analyte determined based on the first response signal, a color-coded indicator selected based on the first response signal, a symbol selected based on the first response signal, a graphical representation of the first response signal over a plurality of values of the first voltage signal, and any suitable combination thereof.

In some implementations, the system further comprises a plurality of reference electrodes, each adapted to be electrically coupled to one of the plurality of sample wells, the plurality of reference electrodes including first a reference electrode adapted to be coupled to the first sample well.

In some implementations, each of the plurality of reference electrodes is paired with one of the plurality of counter electrodes.

In some implementations, the sample applied to the electrochemical detector is a liquid sample. The liquid sample may contain bacteria. The bacteria in the sample may be lysed prior to introducing the sample into the multiplexed electrochemical detector.

In another aspect, a system for performing electrochemical analysis comprises means for introducing a sample into a multiplexed electrochemical detector. The multiplexed electrochemical detector comprises a first sample well and a plurality of leads. The first sample well comprises a first plurality of working electrodes each adapted to be electrically coupled to one of the plurality of leads, and the first plurality of working electrodes are adapted to be electrically coupled to a first counter electrode. The system comprises means for applying a first signal to a first lead of the plurality of leads, and means for measuring a first response signal from the first counter electrode while simultaneously applying a substantially fixed potential to each of a first remainder of the plurality of leads. The system comprises means for determining whether a first target analyte is present in the sample based on the first response signal. In some implementations, the multiplexed electrochemical detector further comprises a second sample well. The second sample well comprises a second plurality of working electrodes each adapted to be electrically coupled to one of the first plurality of working electrodes via one of the plurality of leads. Each of the second plurality of working electrodes is adapted to be electrically coupled to a second counter electrode. The system comprises means for applying a second signal to a second lead of the plurality of leads, and means for measuring a second response signal from the second counter electrode while simultaneously applying a substantially fixed potential to each of a second remainder of the plurality of leads. The system comprises means for determining whether a second target analyte is present in the sample based on the second response signal.

In some implementations, the plurality of working electrodes are adapted to be electrically coupled to the first counter electrode by a first fluid portion of the sample that simultaneously contacts each of the first plurality of working electrodes and the first counter electrode. The second plurality of working electrodes are adapted to be electrically coupled to the second counter electrode by a second fluid portion of the sample that simultaneously contacts each of the second plurality of working electrodes and the second counter electrode. The second fluid portion is substantially physically isolated from the first fluid portion during the measuring of the first and second response signals. Each of the plurality of leads is arranged in one of a plurality of rows on a solid support, and each of the first and second sample wells is formed from first and second elongated channels, respectively, that run substantially perpendicular to each of the plurality of rows.

In some implementations, each of the first and second channels comprises hydrophobic and hydrophilic regions.

In some implementations, the electrochemical detector further comprises a first plurality of probes each tethered to one of the first plurality of working electrodes, wherein the first plurality of probes is selected to hybridize with the first target analyte.

In some implementations, the electrochemical detector further comprises a second plurality of probes tethered to one of the second plurality of working electrodes, wherein the second plurality of probes is selected to hybridize with the second target analyte but not the first target analyte.

In some implementations, each of the first and second counter electrodes is coupled to a common potentiostat, and wherein the means for measuring the first and second response signals comprises means for sequentially measuring the first and second response signals using the common potentiostat.

In some implementations, the first counter electrode is coupled to a first potentiostat and second counter electrode is coupled to a second potentiostat, the method further comprising means for sequentially measuring the first and second response signals using the first and second potentiostats, respectively.

In some implementations, the first and second pluralities of working electrodes comprise one or more nanostructured microelectrodes.

In some implementations, the method comprises means for applying to the electrochemical detector an electrochemical reagent comprising $Ru(NH_3)_6^{3+}$ and $Fe(CN)_6^{3-}$.

In some implementations, the first and second pluralities of probes are selected from nucleic acids, peptide nucleic acids, locked nucleic acids, proteins, and peptides.

In some implementations, the means for determining whether the first target analyte is present in the sample comprises means for determining that a magnitude of the first response signal is greater than a threshold value. The system comprises means for providing an indicator of whether the first target analyte is present in the sample, the indicator selected from a magnitude of the first response signal, a concentration of the first target analyte determined based on the first response signal, a color-coded indicator selected based on the first response signal, a symbol selected based on the first response signal, a graphical representation of the first response signal over a plurality of values of the first voltage signal, and any suitable combination thereof.

In some implementations, the sample is a liquid sample. The liquid sample may contain bacteria. The system comprises means for lysing the bacteria in the sample prior to introducing the sample into the multiplexed electrochemical detector.

In some implementations, the substantially fixed potential is selected to reduce current flow from the first remainder of the plurality of leads to the first counter electrode. In some implementations, the substantially fixed potential corresponds to a ground potential.

Variations and modifications of these embodiments will occur to those of skill in the art after reviewing this disclosure. The foregoing features and aspects may be implemented, in any combination and subcombinations (including multiple dependent combinations and subcombinations), with one or more other features described herein. The various features described or illustrated above, including any components

BRIEF DESCRIPTION OF THE DRAWINGS

The foregoing and other objects and advantages will be apparent upon consideration of the following detailed description, taken in conjunction with the accompanying drawings, in which like reference characters refer to like parts throughout, and in which:

FIG. 6 shows a table comparing the minimum number of contacts used in a standard liquid multiplexer to the minimum number of contacts, according to some implementations;

FIG. 9 depicts a detection unit using a nanostructured microelectrode for electrochemical detection of a nucleotide strand, in accordance with an implementation;

FIG. 10 shows illustrative detection circuitry;

FIGS. 12A-12C demonstrate the electrical isolation of the sample wells, according to an implementation;

FIGS. 15A-15E show multiplexed detection of multiple targets, according to an implementation.

DETAILED DESCRIPTION

To provide an overall understanding of the systems, devices, and methods described herein, certain illustrative implementations will be described. It is to be understood that the systems, devices, and methods disclosed herein, while shown for use in diagnostic systems for the detection of biological disease markers, may be applied to other systems that require multiplexed electrochemical analysis.

Figure 1A:
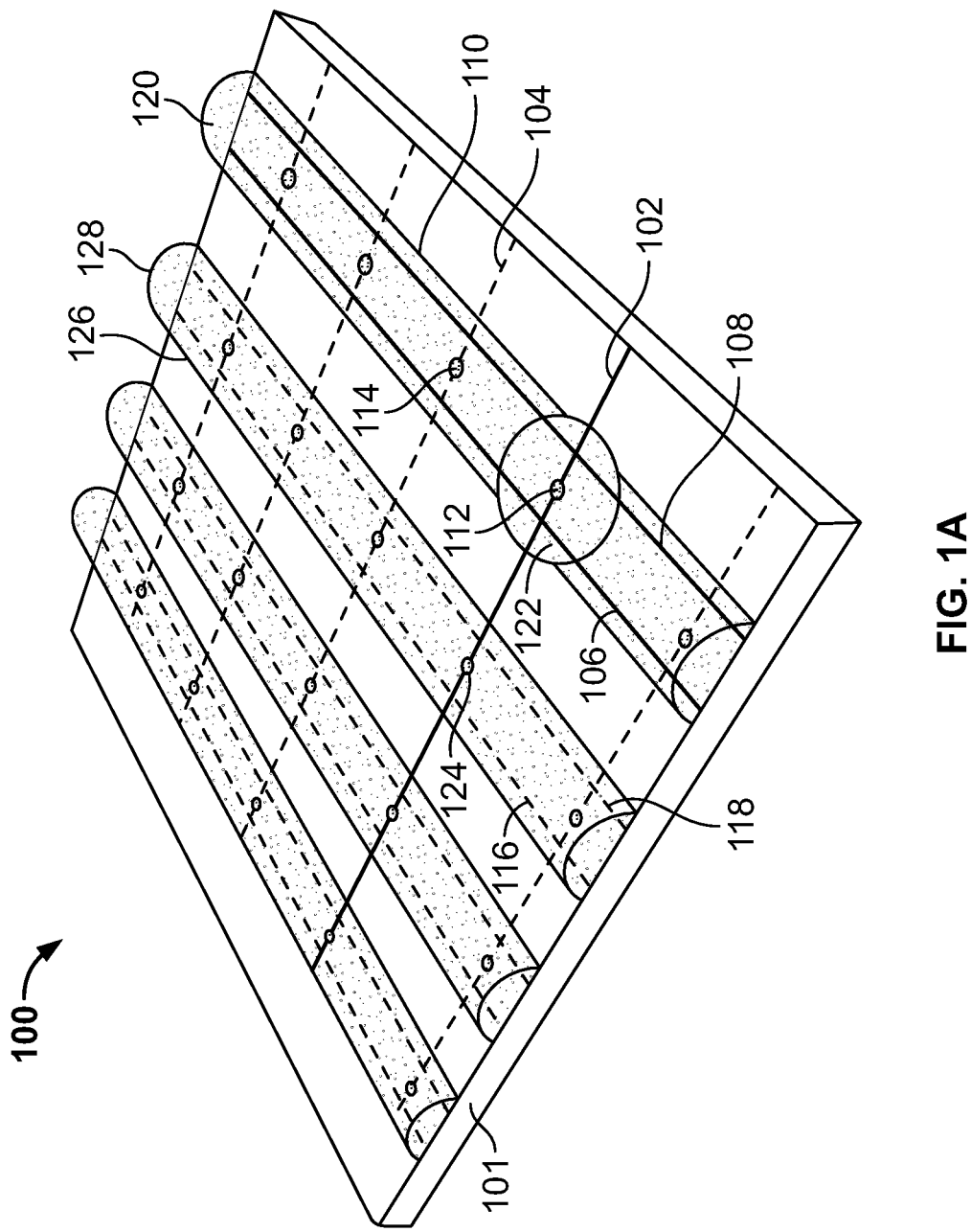
FIGS. 1A and 1B depict the operation of an illustrative multiplexed electrochemical detector.

FIG. 1A shows an illustrative multiplexed electrochemical detection chip 100. The chip 100 has a solid support 101 which includes several leads affixed to the surface. A lead can be any electrical interface (e.g. a conductive material) that permits external contact with one or more electrodes. The chip 100 is shown as including a first lead 102 and a second lead 104 for ease of discussion. However, it is understood that any suitable number of leads can be used. The chip 100 also has a plurality of counter electrodes, including a first counter electrode 106 and a second counter electrode 116, that run substantially perpendicular to the leads. Each counter electrode is the chip 100 is also paired with a reference electrode. For example, counter electrode 106 is paired with reference electrode 108, and counter electrode 116 is paired with reference electrode 118. Addition of a reference electrode reduces potential shifts and can improve specificity during measurements. However, in some implementations (e.g., where such potential shifts are small), the reference electrode is eliminated to reduce the number of external contacts and the overall size of the chip 100. In the implementation shown in FIGS. 1A and 1B, each of the leads, counter electrodes, and reference electrodes extend along (or across) the solid support 101 without intersecting. For example, each of the leads may rest on the solid support while each of the counter electrodes and reference electrodes may be separated from the leads by an insulating layer. In some implementations, counter electrodes and reference electrodes are housed within sample wells formed on solid support 101. For example, counter electrode 106 and reference electrode 108 are contained within sample well 110, which is depicted in the chip 100 as a channel that extends along the length of counter electrode 106 and reference electrode 108, and runs perpendicular to lead 102 and 104. However, it is understood that that the sample wells (including sample well 110) can be any suitable receptacle for receiving a sample, including without limitation, dots, cavities, drops, droplets, chambers, gels, and the like.

In some implementations, the leads, including leads 102 and 104, are arranged in substantially parallel rows, and each lead is electrically coupled to a two or more working electrodes. In one example, each lead is coupled to 4 or more, 8 or more, 16 or more, 24 or more, 25 or more, 32 or more, 50 or more, or 100 or more working electrodes. The sample wells are configured as channels that are arranged substantially perpendicularly to the rows of leads, which establish electrical communication between a working electrode of each lead and a counter electrode. For example, lead 102 has a working electrode 112 that is accessible to sample well 110, and lead 104 has a working electrode 114 that is also accessible to sample well 110. Working electrode 124 is also in electrical contact with lead 102, and is accessible to sample well 126, but not accessible to sample well 110. The working electrodes may be accessible by a plurality of apertures within each sample well, which will be described in greater detail below. A plurality of channels extends across the surface of the electrochemical detector. The channels are isolated from each other using any suitable means, e.g., physical barriers or surface chemistry designed to prevent fluid from one channel from flowing into another channel, so that each of the plurality of channels can hold a separate portion of a sample, if desired. For example, channel 110 contains liquid sample 120, which extends across the surface of the chip 100. Working electrode 112, counter electrode 106, and reference electrode 108 are each contained within sample well 110 and are in electrical communication with each other due to the conductive path provided by liquid sample 120.

In some implementations, the measurements are performed by activating one or more working electrodes at an intersection of a selected lead and a selected counter electrode by applying a signal to the lead and measuring a response signal using a selected counter electrode. For example, a signal can be applied to lead 102 in order to detect a target marker at working electrode 112. Applying a voltage potential to lead 102 will activate all of the working electrodes in electrical contact with lead 102, including, in the example of chip 100, working electrodes 112 and 124. However, if a current is measured through counter electrode 106 while floating the remaining counter electrodes, signal transduction will be limited to the active region 122 of the selected sensor unit. The applied voltage potential may be any suitable potential capable of producing a measurable response in the presence of clinically-relevant levels of the target analyte. In some implementations, the applied potential is selected based on a reduction window of an electrochemical reagent used in the detection. For example, a signal potential of up to −250 mV may be used for a detection analysis that uses an $Ru^{2+}$-containing electrochemical reagent, and a signal potential of up to 300 mV may be used for a detection analysis that uses a ferrocyanide-containing electrochemical reagent. The applied voltage potential can range from up to 5 V, up to 3 V, up to 2 V, up to 1 V, up to 500 mV, up to 300 mV, up to 200 mV, or up to 100 mV in magnitude, and can be either a positive or negative signal potential.

A response signal that is indicative of the levels or concentration of the target analyte in the sample is then measured in response to applying the voltage potential. As described in detail below, the response signal is produced as a result of a hybridization reaction between the target analyte (if present) and a probe specific to the target analyte. In order to reduce cross-talk during the measurement, the remaining leads that are in electrical communication with the active lead 102 are held at a substantially fixed potential that reduces cross-talk between these remaining leads and counter electrode 106 while the response signal (e.g., current) is measured through counter electrode 106. A substantially fixed potential can be any potential that is designed to remain at a constant potential, allowing for signal variations that occur due to fluctuations in the physical properties of circuit elements (e.g., leakage and other circuit losses). For example, the fixed potential may vary by about ±0.001 V to about ±0.002 V or by about ±0.001 V to about ±0.01V, depending on the control circuitry elements, configuration used, and the sensitivity desired. The substantially fixed potential may be a substantially zero potential (i.e., ground), or any other potential that reduces current flow between the working electrodes of the remaining leads to counter electrode 106. In some embodiments, all of the remaining leads are held at a potential that corresponds to a ground potential, or within a range of ground. In some embodiments, the substantially fixed potential applied to each of the remaining leads or a particular subset of the remaining leads is different from that of others, if desired.

Figure 1B:
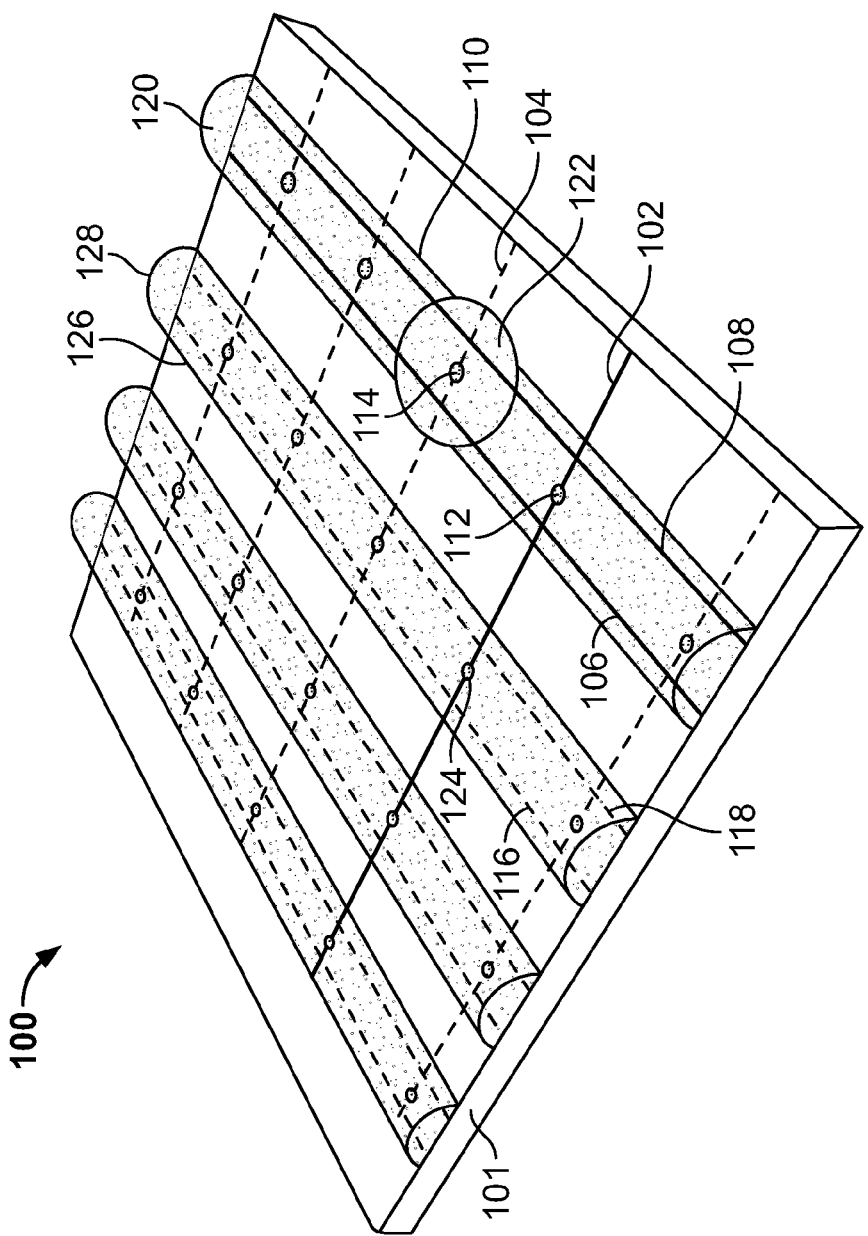

FIG. 1B shows the same chip 100, except that now a measurement is being performed at an active region 130 of a different sensor unit. Lead 104 is now activated, and a response signal is measured at counter electrode 106 while the remaining leads, including lead 102, are simultaneously held at a substantially fixed potential. In some implementations, all other counter electrodes are floated while the response signal is measured through counter electrode 106. This would allow for sequential measurements of targets at various working electrodes by sequentially applying a signal to each of the leads while measuring a response signal at each of the counter electrodes. In some implementations, current is measured at all counter-electrodes simultaneously, while a single lead is activated. For example, suppose lead 102 is activated, as shown in FIG. 1A. In this configuration, for example, a first response signal can be measured at counter electrode 106, which corresponds to a sample analysis at working electrode 112, and a second response signal is measured at counter electrode 116, which corresponds to a sample analysis at working electrode 124. Measurements can be performed simultaneously in this way without cross-talk due to the isolation provided by having the sample separated into different sample wells.

Figure 2A:
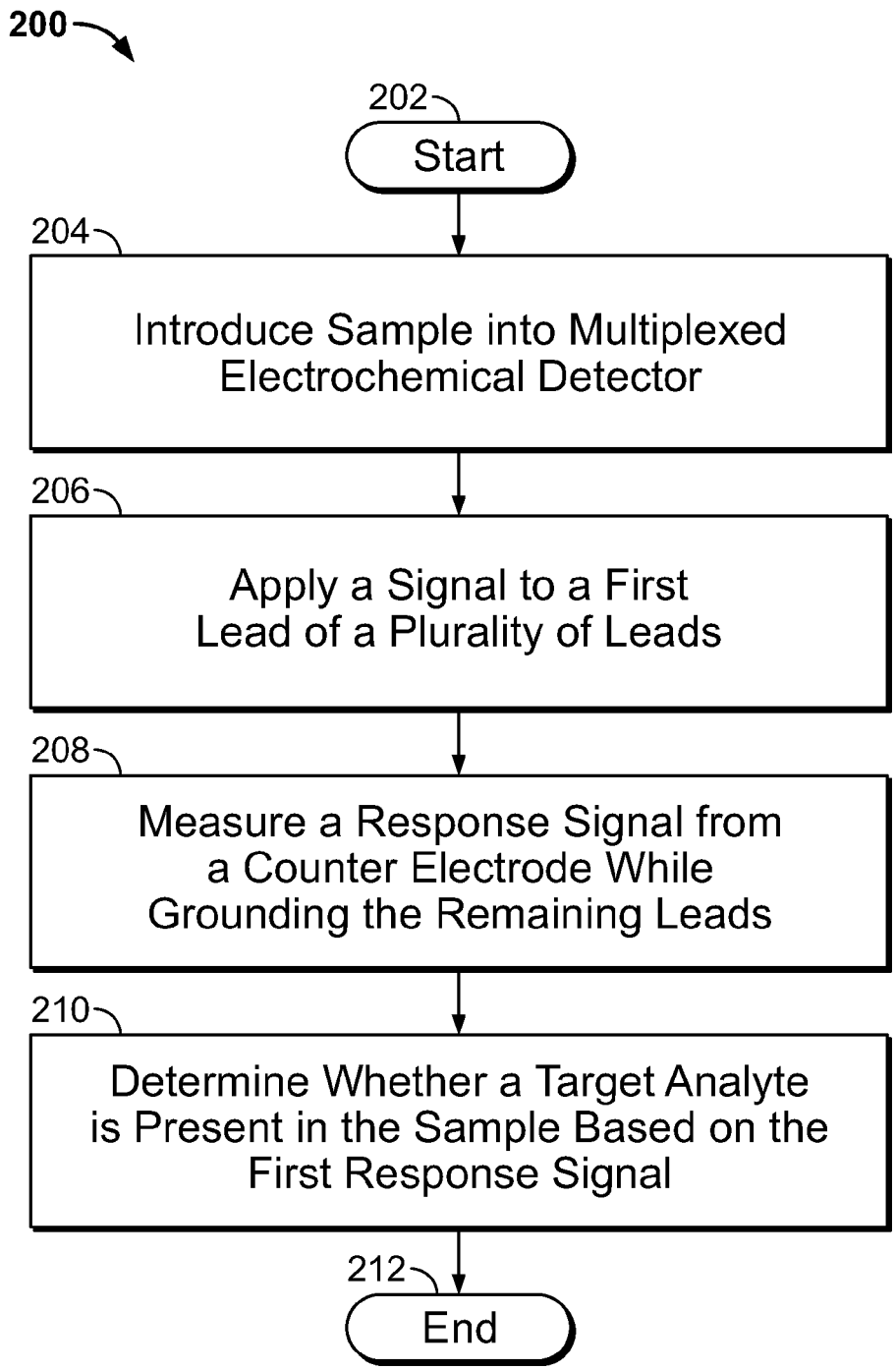
FIGS. 2A and 2B show performing multiplexed detection of target analytes, according to an implementation.

FIG. 2A shows an illustrative process 200 by which a single target marker could be analyzed using the chip 100 of FIG. 1A. The process begins at step 202, which may include any suitable pre-processing or preparation steps such as assembling the electrochemical detector from a component kit or functionalizing the electrodes with biosensor probes as discussed below in FIG. 2B. At step 204, a sample is introduced into the chip 100. The sample may be a liquid or fluid sample including any suitable combination of one or more molecules such as tissue, cells, proteins, fluid, genetic material, bacterial matter or viral matter, plant matter, animal matter, cultured cells, or other organisms or hosts. The sample may contain biological markers indicative of a particular disease or pathogen, as will be described in greater detail below. The sample may be loaded manually by a pipette, automatically flowed into the chamber using microfluidic or macrofluidic channels, or using any other suitable method. The sample may be introduced into a single channel or may be directed into multiple channels, as shown in FIGS. 1A and 1B, depending on the number of target analytes to be detected. For example, where multiple target analytes are to be detected, the electrodes can be functionalized with probes that are selected to hybridize selectively with the different target analytes, such that each well is configured to detect a different target analyte in the same or different sample. In some implementations, the sample wells are not structurally-defined channels and instead comprise hydrophobic and hydrophilic surface chemistry, which serve to provide isolation between regions in which the sample is to be deposited on the chip 100. For example, if a water-based sample is applied directly to the electrochemical detector of such a surface, the sample will automatically assemble into discrete droplets or discrete channels due to the hydrophobic and hydrophilic surface chemistry. In some implementations, the electrochemical detector has a hydrophobic insulating layer, such as SU-8, polydimethylsiloxane, or teflon, that separates the leads from the counter electrodes and reference electrodes. A mask, such as a parylene mask, may be used to selectively expose portions of the insulating layer to an oxygen plasma, making those exposed portions hydrophilic. The channels are microfabricated onto the surface of the detector. For example, an insulating material, such as SU-8, may be patterned to produce channels that contain the sample. In some implementations, the inside surfaces of the microfabricated channels are hydrophilically activated in order to make containment of a water-based sample within the sample wells favorable.

At step 206, a first signal is applied to a first lead of a plurality of leads using a suitable signal generator, which may be powered by an AC/DC power source or battery. For example, a potentiostat may be used to apply a suitable voltage potential to the first lead, thereby activating the lead. When the lead is activated, each of the plurality of working electrodes on the lead will be activated. If multiple measurements are to be made, the leads may be activated in any suitable order. The signal may any suitable type of signal or waveform. For example, the signal may be a current or voltage of any suitable waveform, including DC, AC, square waves, triangle waves, sawtooth waves, decreasing exponentials, or any other signal capable of producing a response signal in response to a biomolecular stimulus, such as nucleic acid hybridization. In some implementations, the response signal is produced in response to an electrochemical reaction that occurs in response to the biomolecular stimulus.

At step 208, the response signal is measured from a selected counter electrode. For example, a current signal may be measured at a selected counter electrode in response to a target marker located in the vicinity of the activated working electrode. In order to reduce electrical cross-talk from other electrodes that are also connected to the active lead, all other leads that share electrical communication with the first lead are held at a substantially fixed potential during the measurement in order to reduce current flow from such other leads. Thus, all other leads that are electrically coupled to the first lead by a fluid sample, are each held at a substantially fixed potential while the first lead is activated. Applying a substantially fixed potential to each of the electrically-coupled leads significantly reduces current flow between these inactive leads and the selected counter electrode, which in turn reduces cross-talk between the leads and improves the sensitivity of the measurements. In clinical situations, the approach can reduce cross-talk to below measurable levels. The signal measured at the selected counter electrode may be, for example, a current, a voltage, or a charge (Coulomb) measurement. For example, if the response signal is a current signal, a voltage potential may be measured across a resistor that is in series with the counter electrode and subsequently converted into a current.

At step 210, a determination is made, based on the response signal, as to whether a target marker is present in the sample. Any suitable detection mechanism may be used, including, for example, determining whether the amplitude of the response signal exceeds a particular threshold, and concluding that the target is present or absent in the sample based on the comparison. In some implementations, a baseline signal is measured under similar measurement conditions for which it is known that no target is present (as a control), and the baseline signal may be subtracted from the signal measured when the target is believed to be present. After the signal is corrected for the baseline, it is compared to a particular threshold to determine if the target marker is present. The determination may be made using any suitable processing circuitry coupled to the multiplexed detection unit. In some implementations, the electrochemical detector is fabricated as a standalone chip with a plurality of pins. The pins may be arranged in any suitable fashion to interface with an external processor for which quantitative determinations, such as threshold comparisons, can be performed. The electrochemical detector includes a readout device that generates an indicator to communicate the results of the detection. The readout device may be any suitable display device, such as LED indicators, a touch-activated display, an audio output, or any combination of these. Any suitable mechanism for indicating the presence or absence of the target may be used. For example, the indicator may include an amplitude of the first response signal, a concentration of the first target marker determined based on the first response signal, a color-coded indicator selected based on the response signal, a symbol selected based on the a particular response signal, a graphical representation of the response signal over a plurality of values for a corresponding input signal, and any suitable combination thereof.

Figure 2B:
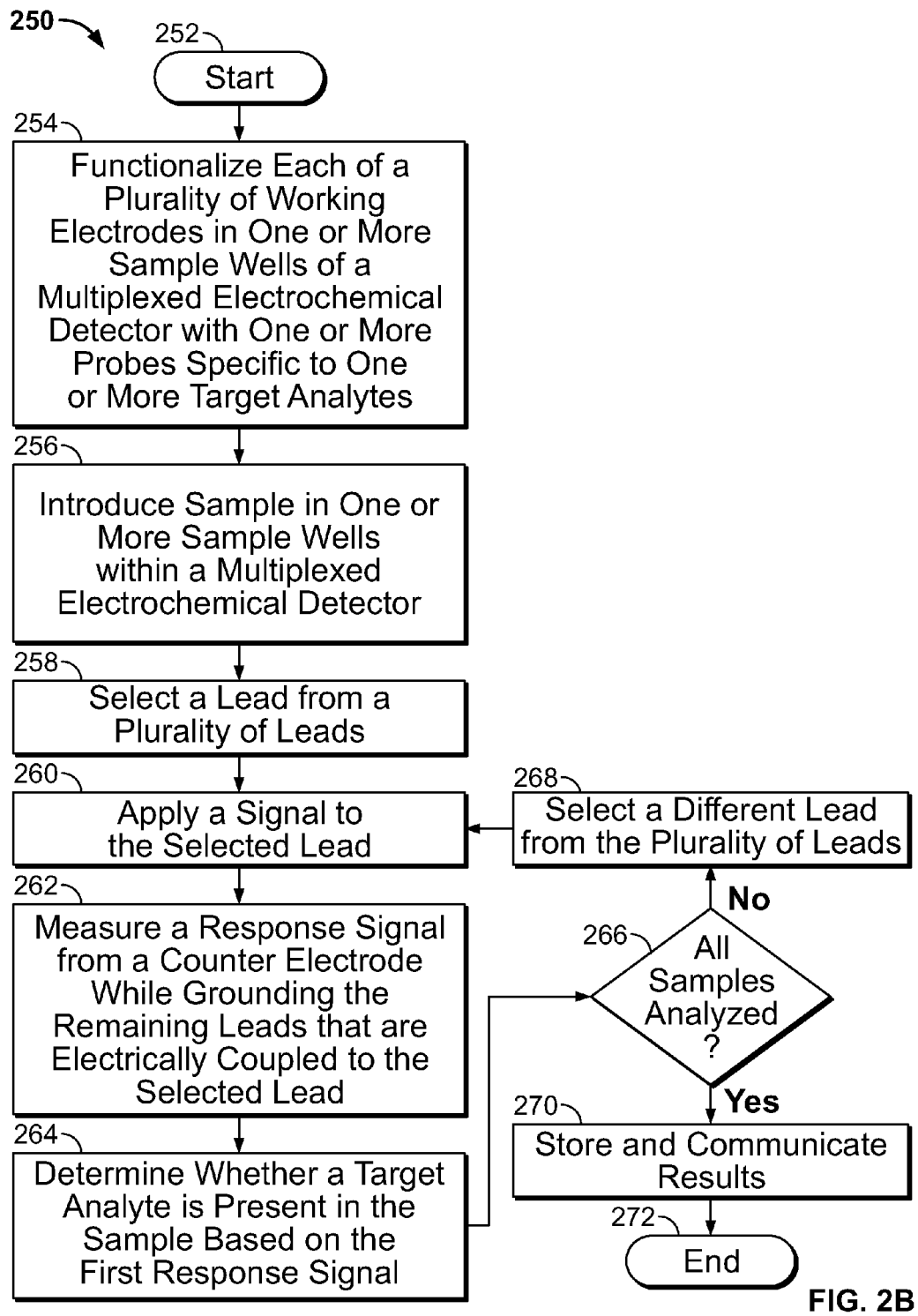

FIG. 2B shows an illustrative process 250 by which multiple target markers can be analyzed in a multiplexed fashion using the chip 100 of FIG. 1A. The process begins at step 252. At step 254, each of a plurality of working electrodes in one or more sample wells within a multiplexed electrochemical detector are functionalized with one or more probe molecules, which are specific to one or more target analytes. In some implementations, the working electrodes are functionalized by placing liquid droplets, each containing a particular probe type, directly on each of the working electrodes. This may be done, for example, manually using a pipette or automatically by a printing device. In some implementations, the sample wells are designed to receive liquid droplets that do not span the entire volume of the sample well, but locally contact a group of working electrodes, resulting in group of working electrodes being functionalized with the same type of probe, while another group of working electrodes are functionalized with different probes. At step 256, a sample is introduced in one or more of the sample wells using any suitable method. At step 258, a lead that is electrically coupled to one or more wells having the sample therein is selected from the plurality of leads, and the process continues to step 260 where a first signal is applied to the selected lead. At step 262, a response signal is measured from a counter electrode coupled to the selected lead, using any suitable method described herein, while applying a substantially fixed potential to each of the remaining of the plurality of leads electrically coupled to the active lead. In some implementations, a response signal is measured at all of the counter electrodes simultaneously. Each counter electrode may be connected to its own potentiostat. In some implementations, more than one counter electrode shares a single potentiostat, each counter electrode may be selected to perform a method sequentially while the remaining counter electrodes are floated.

At step 264, a determination is made as to whether a particular target marker is present in the sample based on a response signal corresponding to the active region of the activated lead and selected counter electrode. The determination is made using any suitable method described herein. In some implementations, as each particular working electrode is analyzed, the resultant response signal is recorded and indexed according to the order in which the input signals are applied, which will be discussed below in greater detail. At step 266, a determination is made as to whether all targets have been analyzed. For example, a processor may determine whether all combinations of leads and counter electrodes have been analyzed. If any lead and counter electrode combinations remain to be analyzed, the process then proceeds to step 268. At step 268, a new lead is selected from the plurality of leads. In some embodiments, the same lead selected previously is selected and a measurement is made at a different counter electrode in step 262. In some implementations, the new lead and new counter electrode are selected in response to determining that this combination of leads and counter electrodes has not been analyzed previously. The process continues to step 260 where a signal is applied to the new lead, and then eventually back to step 266. If it is determined that all working electrodes have been analyzed, the process continues to step 270. At step 270, the results of the analysis are stored and communicated. All measured response signals are stored in a memory and processed so that a suitable readout is generated. In some embodiments, the readout is provided in real-time as response signals are measured for each detection unit of the chip 100. The process ends at step 272.

It should be understood that the above steps of the flow diagrams of FIGS. 2A and 2B may be executed or performed in any order or sequence not limited to the order and sequence shown and described in the figures. Also, some of the above steps of the flow diagrams of FIGS. 9 and 10 may be executed or performed substantially simultaneously, where appropriate.

Figure 3A:
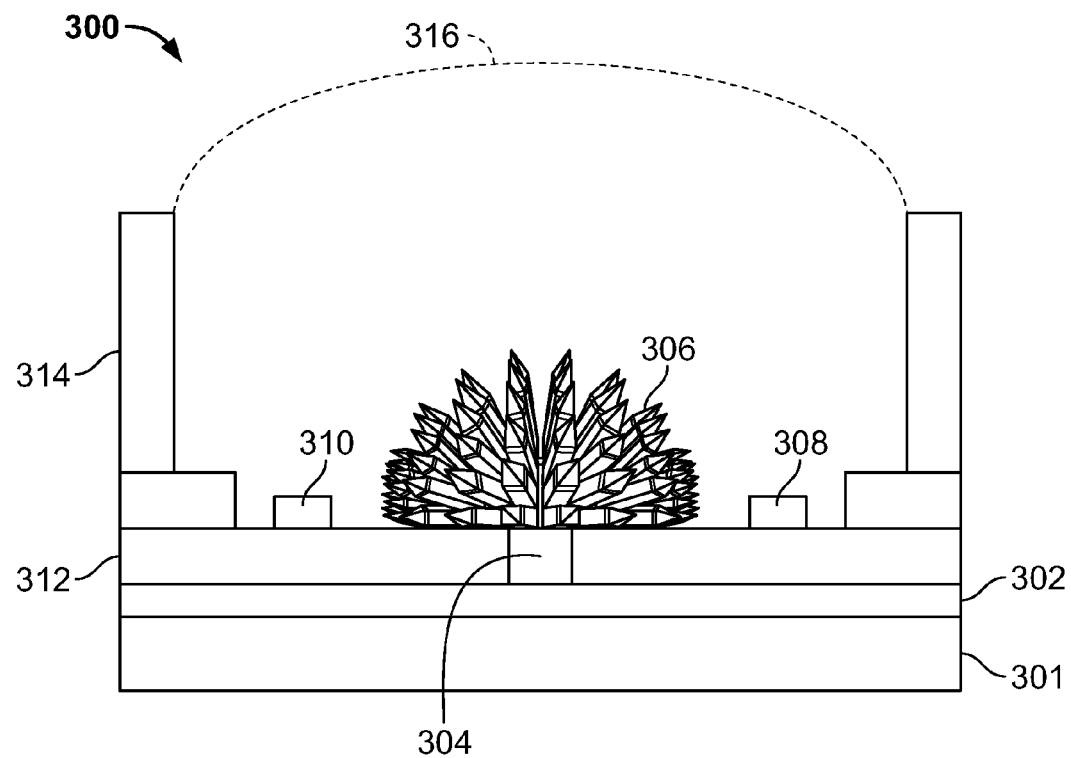
FIGS. 3A and 3B depicts a cross-sectional view of a sensor unit and microscope images of a sample well, according to an implementation.
Figure 3B:
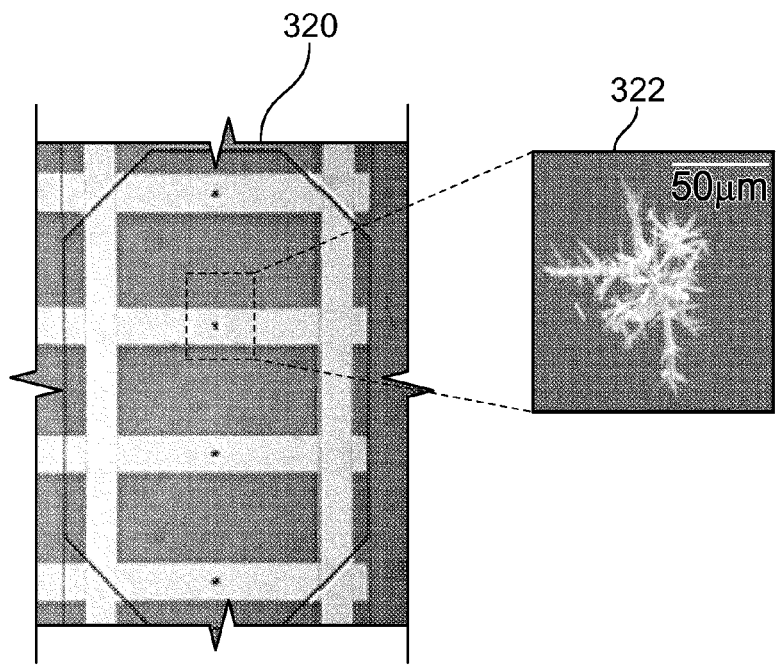

FIGS. 3A and 3B show a cross-sectional view of active region 300 of an exemplary electrochemical detector, including solid support 301, lead 302 (which runs along a first direction of solid support 301), and counter electrode 308 and reference electrode 310, which run perpendicular to the first direction. Solid support 301 may be a non-conducting material, such as a glass substrate or a silicon chip with an insulating oxide layer. Lead 302 is a conductive material that is affixed to solid support 301, and may be one of a plurality of leads that are arranged in substantially parallel rows, as shown in FIGS. 1A and 1B. Lead 302 is a lithographically defined gold electrode that adheres to solid support 301 by a thin chrome layer. Insulating layer 312 covers lead 302, which has an aperture 304 that passes through insulating layer 312 down to lead 302. Counter electrode 308 and reference electrode 310, which run in substantially parallel columns, are lithographically defined and deposited onto insulating layer 312. The rows and columns can run in any direction, with the rows being substantially perpendicular to the columns. Working electrode 306 may be a nanostructured microelectrode in electrical contact with lead 302, which extends from lead 302 through aperture 304 and is accessible to a sample contained within sample well 314. Working electrode 306 may be deposited into aperture 304 using methods discussed in detail below. In some implementations, the working electrode is the exposed portion of the lead rather than a nanostructured microelectrode. In some implementations, a two-electrode active region is formed by eliminating reference electrode 310.

The sample well 314 is formed from an insulating layer that extends from the surface of insulating layer 312, which allows sample well 314 to contain fluid sample 316. When fluid sample 316 is in sample well 314, working electrode 306, counter electrode 308, and reference electrode 310 are electrically coupled due to the conductivity of fluid sample 316. In some implementations, the sample well is defined by patterning hydrophobic and hydrophilic regions onto insulating layer 312 rather than structurally defining sample well 312. In some implementations, the interior portion of sample well 314, which houses sample 316, is hydrophilic. In some implementations, the leads, counter electrodes, and working electrodes are defined on different layers. For example, counter electrode 308 and reference electrode 310 may be affixed to solid support 301, while lead 304 is affixed to insulating layer 312.

FIG. 3B shows a microscope image 320 of a top-down view of an electrochemical detector, according to an implementation. For each lead shown, 5 micrometer (μm) wide apertures were defined. Electron micrograph 322 shows a close-up view of a nanostructured microelectrode that serves as a working electrode.

Figure 4:
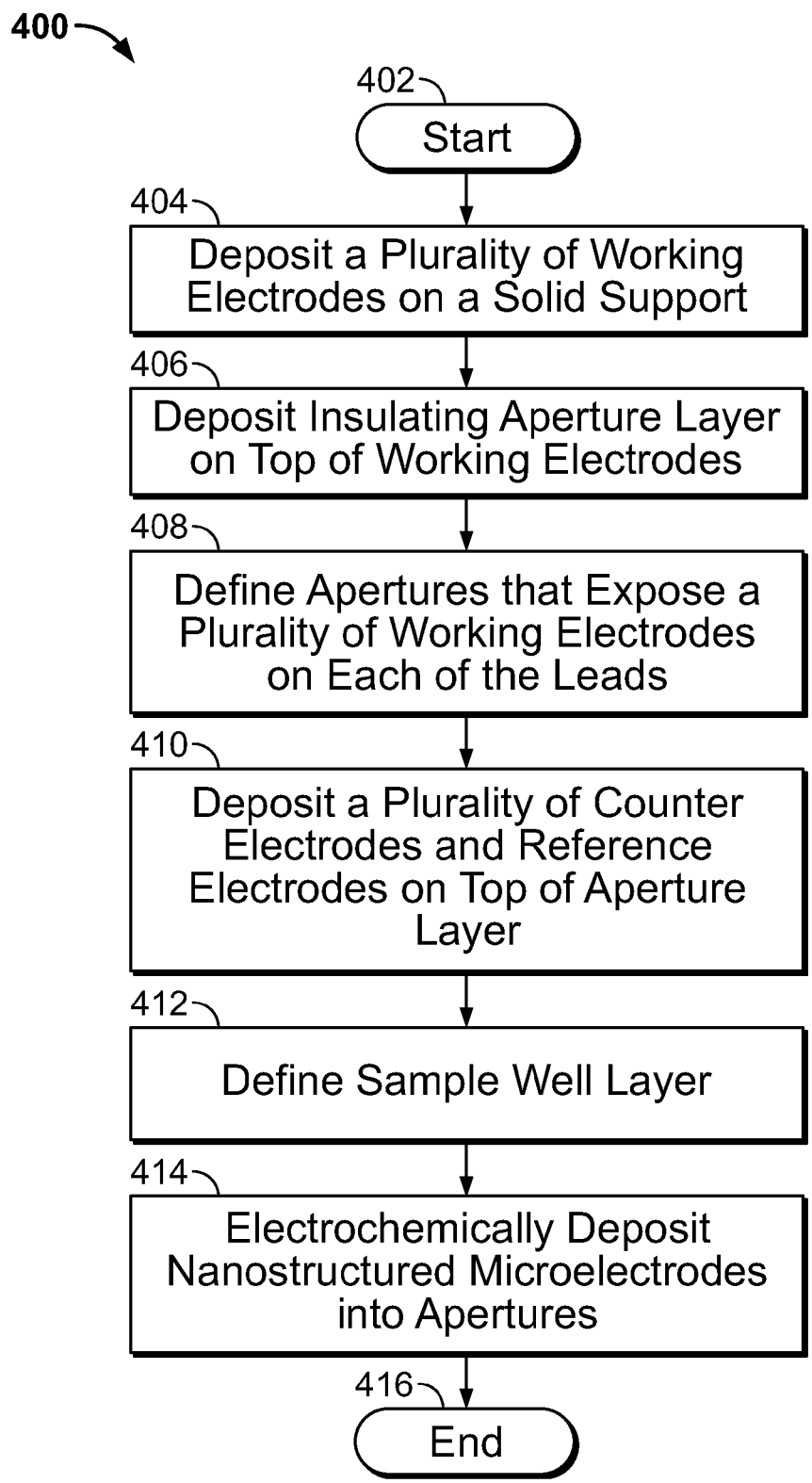
FIG. 4 show fabricating an exemplary multiplexed electrochemical detector, according to an implementation.

FIG. 4 shows an illustrative process for fabricating an electrochemical detector. The process begins at step 402. At step 404, a plurality of leads are deposited on a solid support. In some implementations, a glass substrate is used as a solid support. The leads can be defined using any suitable lithographic technique. For example, standard contact lithography using AZ1600 photoresist may be used to define the leads, followed by deposition of a 5 nanometer (nm) chrome layer followed by a 50 nm gold layer. Wet etchants may also be applied following removal of the positive photoresist. After the leads are defined, the process proceeds to step 406. At step 406, an insulating aperture layer is deposited on top of the leads. In some implementations, a negative photoresist, such as SU-8 2002, is used as the insulating layer by spin-coating onto the solid support. Apertures that extend to the leads can then be lithographically defined. At step 410, a plurality of counter electrodes and reference electrodes are deposited on top of the aperture layer. Lithographic methods similar to those used to deposit the leads on the solid support may be used to deposit the counter electrodes and reference electrodes. At step 412, a sample well layer may be defined. For example, negative photoresists, such as SU-8 2002 and SU-8 3025, may be used to define the sample well layer. In some implementations, the sample wells are made to be hydrophilic using, for example, $O_2$ plasma etching. At step 414, nanostructured microelectrodes may be deposited into the apertures, resulting in working electrodes with high surface areas. In some implementations, the nanostructured microelectrodes are deposited by electroplating in a solution of 50 mM $HAuCl_4$ and 0.5 M HCl at 0 mV for 60 seconds. Additional platinum coating is also performed by electroplating in a solution of 5 mM $PdCl_2$ and $HClO_4$ at −250 mV for 10 seconds. The process ends at step 416.

FIGS. 5A-5E illustrate multiplexed selection of a particular sensor unit in an illustrative electrochemical detection system. The exemplary chip shown in FIG. 5A has 4 rows and 4 columns for a total of 16 detection units. However, any suitable combination of rows, columns, and detection units may be used. Each row has a lead for which electrical contact can be made externally, and each comprises 4 working electrodes. Each column contains a portion of a liquid sample, which establishes electrical communication between a counter electrode that passes through the liquid sample and one working electrode of each of the leads. Electrical contact can be made externally with each of the 4 reference electrodes, A particular detection unit can be selected by applying a driving signal to a particular lead and measuring a response signal at a particular counter electrode. In some implementations, the remaining counter electrodes are floated (i.e. opened) to prevent current flow from the lead to the remaining counter electrodes.

Figure 5A:
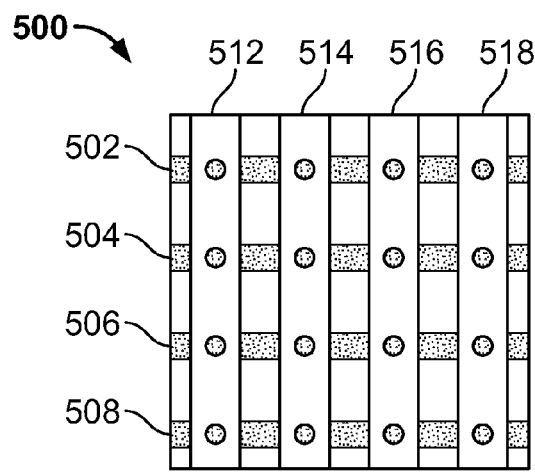
FIGS. 5A-5E illustrate multiplexed selection of a particular sensor unit in an illustrative electrochemical detection system.
Figure 5B:
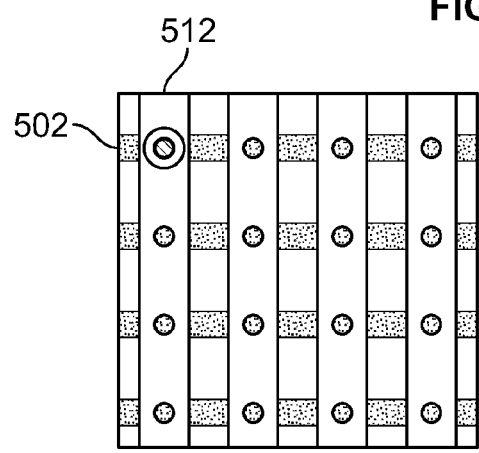
Figure 5C:
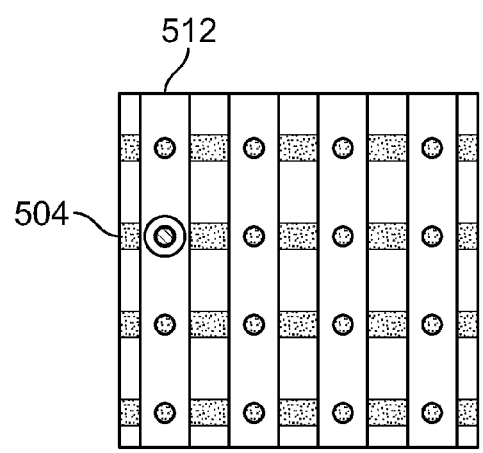
Figure 5D:
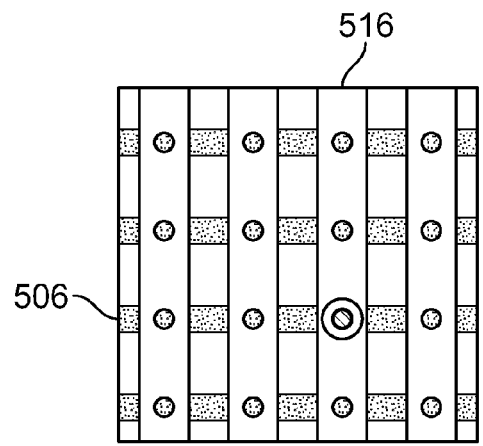
Figure 5E:
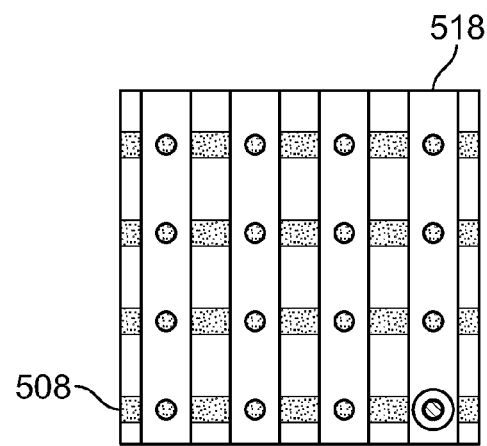

FIGS. 5B-5E illustrate the selection of a particular detection unit by selecting a lead (row) and a counter electrode (column) in one configuration that may be used to detect multiple target analytes. In FIG. 5B, a signal is applied to lead 502 in row 1, and a response signal is measured at counter electrode 512 in column 1, while leads 504, 506, and 508 are each held at a substantially fixed potential. The response signal can be indicative of the presence or absence of a first target analyte for which the working electrode 520 has been specifically functionalized (e.g. by attachment of a target-specific probe) to detect. Similarly, in FIG. 5C, a signal is applied to lead 504 in row 2, and a response signal is measured at counter electrode 512 in column 1, while leads 502, 506, and 508 are each held at a substantially fixed potential. The response signal can be indicative of the presence or absence of a second target analyte for which the working electrode 522 has been specifically functionalized (e.g., by attachment of a target-specific probe) to detect. In FIG. 5D, a signal is applied to lead 506 in row 3, and a response signal is measured at counter electrode 516 in column 3 while leads 502, 504, and 508 are each held at a substantially fixed potential. In FIG. 5E, a signal is applied to lead 508 in row 4, and a response signal is measured at counter electrode 518 in column 4, while leads 502, 504, and 506 are each held at a substantially fixed potential. Working electrodes 524 and 526 in FIGS. 5D and 5E can be functionalized to detect third and fourth target analytes, respectively, which target analytes differ from the first and second targets. In each of the configurations illustrated in FIGS. 5B-5E, the fixed potentials may vary from lead to lead, or may be the same for some or all leads. The signal applied to the selected lead the applied potential for each of the remaining leads may vary depending on the reagent conditions of each sample well. For example, each sample well may contain a different electrochemical reagent that requires a different potential window. In this manner, the chip 100 can be used to detect multiple target analytes from the same sample stock or from different samples by individually addressing and reading the electrodes in a sequential fashion. It is understood that the selection of rows and columns may be performed suitable order.

FIG. 6 shows a table comparing the minimum number of contacts used in a standard serially-connected multiplexer to the minimum number of contacts used in the implementations described herein. The use of separated liquid channels allows for the sharing of a single reference electrode among multiple leads. Accordingly, the pinout for addressing a large array of sensor units is dramatically reduced compared to a serially-connected chip design. For example, a serially-connected chip arranged in an array of 10 rows and 10 columns would require 100 contacts to address each of the 100 sensor units, with two additional shared counter and reference electrode contacts, respectively. A channel-based electrochemical chip, as described herein, could have as few as 10 contacts for 10 leads, 10 contacts for 10 shared counter electrodes, and 10 contacts for the optional reference electrodes. Each counter electrode has an isolated sample well that establishes electrical contact between each counter electrode with one working electrode on each of the 10 leads, resulting in a total of 100 sensor units. Thus, 20 total contacts would be sufficient for a two-electrode system, and 30 total contacts for a three-electrode system. Generally, if N is the total number of sensor units, then a serially-connected chip would require N contacts, while an electrochemical chip described herein would require only $2\sqrt{N}$ (two times the square-root of the number of sensor units) for a two-electrode system and $3\sqrt{N}$ (three times the square-root of the number of sensor units) for a three-electrode system. This reduction of contacts greatly reduces the overall size of the chip. Use of liquid-based contacts allows for a simpler connection strategy, and is ultimately more cost effective than a serially-connected chip or other multiplexed chips that employ passive switching.

Figure 7:
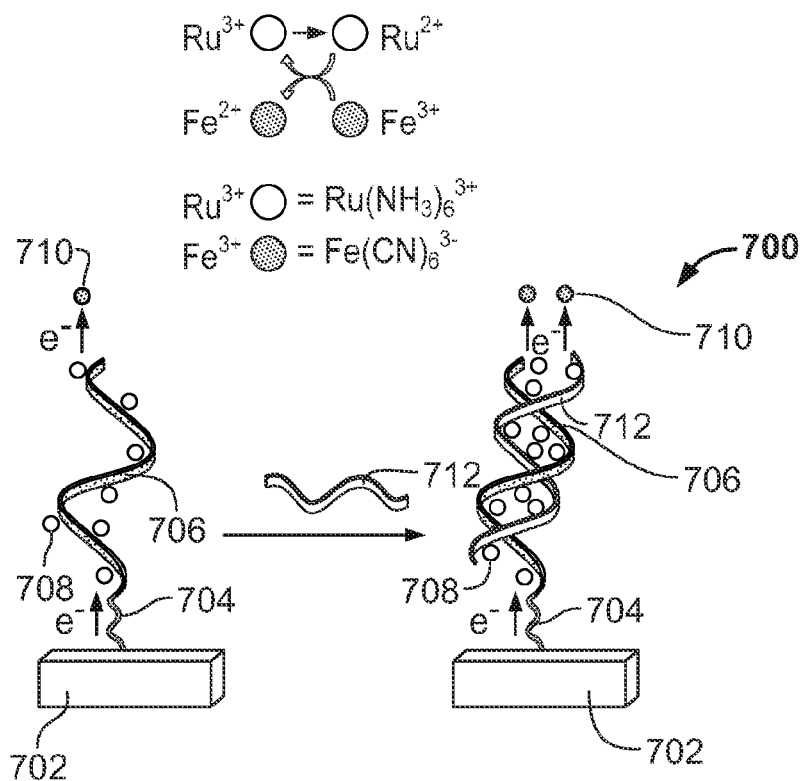
FIG. 7 depicts electrochemical detection of a nucleotide strand, according to an implementation.

FIGS. 7 and 8A-8D depict illustrative tools, sensors, biosensors, and techniques for detecting target analytes, including cellular, molecular, or tissue components, by electrochemical methods. FIG. 7 depicts electrochemical detection of a nucleotide strand using a biosensor system. System 700 includes an electrode 702 with an associated probe 706 attached to the electrode 702 via a linker 704. Electrode 702 can be any of the working electrodes of chip 100. The probe 706 is a molecule or group of molecules, such as nucleic acids (e.g., DNA, RNA, cDNA, mRNA, rRNA, etc.), oligonucleotides, peptide nucleic acids (PNA), locked nucleic acids, proteins (e.g., antibodies, enzymes, etc.), or peptides, that is able to bind to or otherwise interact with a biomarker target (e.g., receptor, ligand) to provide an indication of the presence of the ligand or receptor in a sample. The linker 704 is a molecule or group of molecules which tethers the probe 706 to the electrode 702, for example, through a chemical bond, such as a thiol bond.

In some implementations, the probe 706 is a polynucleotide capable of binding to a target nucleic acid sequence through one or more types of chemical bonds, such as complementary base pairing and hydrogen bond formation. This binding is also called hybridization or annealing. For example, the probe 706 may include naturally occurring nucleotide and nucleoside bases, such as adenine (A), guanine (G), cytosine (C), thymine (T), and uracil (U), or modified bases, such as 7-deazaguanosine and inosine. The bases in probe 706 can be joined by a phosphodiester bond (e.g., DNA and RNA molecules), or with other types of bonds. For example, the probe 706 can be a peptide nucleic acid (PNA) oligomer in which the constituent bases are joined by peptide bonds rather than phosphodiester linkages. A peptide nucleic acid (PNA) oligomer may contain a backbone comprised of N-(2-aminoethyl)-glycine units linked by peptide bonds. Peptide nucleic acids have a higher binding affinity and increased specificity to complementary nucleic acid oligomers, and accordingly, may be particularly beneficial in diagnostic and other sensing applications, as described herein.

In some implementations, the probe 706 has a sequence partially or completely complementary to a target marker 712, such as a nucleic acid sequence sought. Target marker 712 is a molecule for detection, as will be described in further detail below. In some implementations, probe 706 is a single-stranded oligonucleotide capable of binding to at least a portion of a target nucleic acid sought to be detected. In certain approaches, the probe 706 has regions which are not complementary to a target sequence, for example, to adjust hybridization between strands or to serve as a non-sense or negative control during an assay. The probe 706 may also contain other features, such as longitudinal spacers, double-stranded regions, single-stranded regions, poly(T) linkers, and double stranded duplexes as rigid linkers and PEG spacers. In certain approaches, electrode 702, can be configured with multiple, different probes 706 for multiple, different targets 712.

The probe 706 includes a linker 704 that facilitates binding of the probe 706 to the electrode 702. In certain approaches, the linker 704 is associated with the probe 706 and binds to the electrode 702. For example, the linker 704 may be a functional group, such as a thiol, dithiol, amine, carboxylic acid, or amino group. For example, it may be 4-mercaptobenzoic acid coupled to a 5' end of a polynucleotide probe. In certain approaches, the linker 704 is associated with the electrode 702 and binds to the probe 706. For example, the electrode 702 may include an amine, silane, or siloxane functional group. In certain approaches, the linker 704 is independent of the electrode 702 and the probe 706. For example, linker 704 may be a molecule in solution that binds to both the electrode 702 and the probe 706.

Under appropriate conditions, such as in a suitable hybridization buffer, the probe 706 can hybridize to a complementary target marker 712 to provide an indication of the presence of target marker 712 in a sample. In certain approaches, the sample is a biological sample from a biological host. For example, a sample may be tissue, cells, proteins, fluid, genetic material, bacterial matter or viral matter, plant matter, animal matter, cultured cells, or other organisms or hosts. The sample may be a whole organism or a subset of its tissues, cells or component parts, and may include cellular or noncellular biological material. Fluids and tissues may include, but are not limited to, blood, plasma, serum, cerebrospinal fluid, lymph, tears, saliva, blood, mucus, lymphatic fluid, synovial fluid, cerebrospinal fluid, amniotic fluid, amniotic cord blood, urine, vaginal fluid, semen, tears, milk, and tissue sections. The sample may contain nucleic acids, such as deoxyribonucleic acids (DNA), ribonucleic acids (RNA), or copolymers of deoxyribonucleic acids and ribonucleic acids or combinations thereof. In certain approaches, the target marker 712 is a nucleic acid sequence that is known to be unique to the host, pathogen, disease, or trait, and the probe 704 provides a complementary sequence to the sequence of the target marker 712 to allow for detection of the host sequence in the sample.

In certain aspects, systems, devices and methods are provided to perform processing steps, such as purification and extraction, on the sample. Analytes or target molecules for detection, such as nucleic acids, may be sequestered inside of cells, bacteria, or viruses. The sample may be processed to separate, isolate, or otherwise make accessible, various components, tissues, cells, fractions, and molecules included in the sample. Processing steps may include, but are not limited to, purification, homogenization, lysing, and extraction steps.

The processing steps may separate, isolate, or otherwise make accessible a target marker, such as the target marker 712 in or from the sample.

In certain approaches, the target marker 712 is genetic material in the form of DNA or RNA obtained from any naturally occurring prokaryotes such, pathogenic or non-pathogenic bacteria (e.g., *Escherichia, Salmonella, Clostridium, Chlamydia*, etc.), eukaryotes (e.g., protozoans, parasites, fungi, and yeast), viruses (e.g., Herpes viruses, HIV, influenza virus, Epstein-Barr virus, hepatitis B virus, etc.), plants, insects, and animals, including humans and cells in tissue culture. Target nucleic acids from these sources may, for example, be found in biological samples of a bodily fluid from an animal, including a human. In certain approaches, the sample is obtained from a biological host, such as a human patient, and includes non-human material or organisms, such as bacteria, viruses, other pathogens.

A target nucleic acid molecule, such as target marker 712, may optionally be amplified prior to detection. The target nucleic acid can be in a double-stranded or single-stranded form. A double-stranded form may be treated with a denaturation agent to render the two strands into a single-stranded form, or partially single-stranded form, at the start of the amplification reaction, by methods such as heating, alkali treatment, or by enzymatic treatment.

Once the sample has been treated to expose a target nucleic acid, e.g., target molecule 712, the sample solution can be tested as described herein to detect hybridization between probe 706 and target molecule 712. For example, electrochemical detection may be applied as will be described in greater detail below. If target molecule 712 is not present in the sample, the systems, device, and methods described herein may detect the absence of the target molecule. For example, in the case of diagnosing a bacterial pathogen, such as *Chlamydia trachomatis*, the presence in the sample of a target molecule, such as an RNA sequence from *Chlamydia trachomatis*, would indicate presence of the bacteria in the biological host (e.g., a human patient), and the absence of the target molecule in the sample indicates that the host is not infected with *Chlamydia trachomatis*. Similarly, other markers may be used for other pathogens and diseases.

Referring to FIG. 7, the probe 706 of the system 700 hybridizes to a complementary target molecule 712. In certain approaches, the hybridization is through complementary base pairing. In certain approaches, mismatches or imperfect hybridization may also take place. "Mismatch" typically refers to pairing of noncomplementary nucleotide bases between two different nucleic acid strands (e.g., probe and target) during hybridization. Complementary pairing is commonly accepted to be A-T, A-U, and C-G. Conditions of the local environment, such as ionic strength, temperature, and pH can effect the extent to which mismatches between bases may occur, which may also be termed the "specificity" or the "stringency" of the hybridization. Other factors, such as the length of a nucleotide sequence and type of probe, can also affect the specificity of hybridization. For example, longer nucleic acid probes have a higher tolerance for mismatches than shorter nucleic acid probes. In general, protein nucleic acid probes provide higher specificity than corresponding DNA or RNA probes.

As illustrated in the figures, the presence or absence of target marker 712 in the sample is determined through electrochemical techniques. These electrochemical techniques allow for the detection of extremely low levels of nucleic acid molecules, such as a target RNA molecule obtained from a biological host. Applications of electrochemical techniques are described in further detail in U.S. Pat. Nos. 7,361,470 and 7,741,033, and PCT Application No. PCT/US12/024,015, which are hereby incorporated by reference herein in their entireties. A brief description of these techniques, as applied to the current system, is provided below, it being understood that the electrochemical techniques are illustrative and non-limiting and that other techniques can be envisaged for use with the other systems, devices and methods of the current system.

In the electrochemical application of FIG. 7, a solution sample is applied to the working electrode 702. In practice, a redox pair having a first transition metal complex 708 and a second transition metal complex 710 is added to the sample solution. A signal generator or potentiostat is used to apply an electrical signal to the working electrode 702, causing the first transition metal complex 708 to change oxidative states, due to its close association with the working electrode 702 and the probe 706. Electrons can then be transferred to the second transition metal complex 710, creating a current through the working electrode 702, through the sample, and back to the signal generator. The current signal is amplified by the presence of the first transition metal complex 708 and the second transition metal complex 710, as will be described below.

The first transition metal complex 708 and the second transition metal complex 710 together form an electrochemical reporter system which amplifies the signal. A transition metal complex is a structure composed of a central transition metal atom or ion, generally a cation, surrounded by a number of negatively charged or neutral ligands possessing lone pairs of electrons that can be transferred to the central transition metal. A transition metal complex (e.g., complexes 708 and 710) includes a transition metal element found between the Group IIA elements and the Group IIB elements in the periodic table. In certain approaches, the transition metal is an element from the fourth, fifth, or sixth periods between the Group IIA elements and the Group IIB elements of the periodic table of elements. In some implementations, the first transition metal complex 708 and second transition metal complex 710 include a transition metal selected from the group comprising cobalt, iron, molybdenum, osmium, ruthenium and rhenium. In some implementations, the ligands of the first transition metal complex 708 and second transition metal complex 710 is selected from the group comprising pyridine-based ligands, phenathroline-based ligands, heterocyclic ligands, aqua ligands, aromatic ligands, chloride ($Cl^-$), ammonia ($NH_3^+$), or cyanide ($CN^-$). In certain approaches, the first transition metal complex 108 is a transition metal ammonium complex. For example, as shown in FIG. 7, the first transition metal complex 108 is $Ru(NH_3)_6^{3+}$. In certain approaches, the second transition metal complex 710 is a transition metal cyanate complex. For example, as shown in FIG. 7, the second transition metal complex is $Fe(CN)_6^{3-}$. In certain approaches, the second transition metal complex 710 is an iridium chloride complex such as $IrCl_6^{2-}$ or $IrCl_6^{3-}$.

In certain applications, if the target molecule 712 is present in the sample solution, the target molecule 12 will hybridize with the probe 706, as shown on the right side of FIG. 7. The first transition metal complex 108 (e.g., $Ru(NH_3)_6^{31}$) is cationic and accumulates, due to electrostatic attraction forces as the nucleic acid target molecule 712 hybridizes at the probe 706. The second transition metal complex 710 (e.g., $Fe(CN)_6^{3-}$) is anionic and is repelled from the hybridized target molecule 712 and probe 706. A signal generator, such as a potentiostat, is used to apply a voltage signal to the electrode. As the signal is applied, the first transition metal complex 708 is reduced (e.g., from $Ru(NH_3)_6^{3+}$ to $Ru(NH_3)_6^{2+}$). The reduction of the second metal complex 710 (e.g., $Fe(CN)_6^{3-}$) is more thermodynamically favorable, and accordingly, electrons (e⁻) are shuttled from the reduced form of the first transition metal complex 708 to the second transition metal complex 710 to reduce the second transition metal complex (e.g., $Fe(CN)_6^{3-}$ to $Fe(CN)_6^{4-}$) and regenerate the original first transition metal complex 708 (e.g., $Ru(NH_3)_6^{3+}$). This catalytic shuttling process allows increased electron flow through the working electrode 702 when the potential is applied, and amplifies the response signal (e.g., a current), when the target molecule 712 is present. When the target molecule 712 is absent from the sample, the measured signal is significantly reduced.

Figure 8:
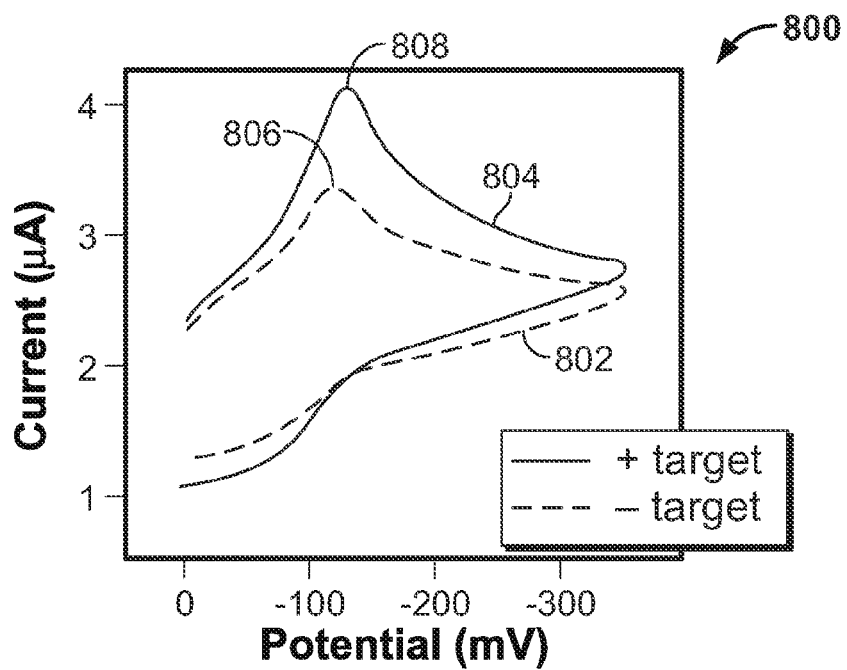
FIG. 8 depicts electrochemical detection signals, according to an implementation.

Chart 800 of FIG. 8 depicts representative electrochemical detection signals. A signal generator such as a potentiostat, is used to apply a voltage signal at an electrode, such as working electrode 702 of FIG. 7. Electrochemical techniques including, but not limited to cyclic voltammetry, amperometry, chronoamperometry, differential pulse voltammetry, calorimetry, and potentiometry may be used for detecting a target marker. In certain approaches, an applied potential or voltage is altered over time. For example, the potential may be cycled or ramped between two voltage points, such from 0 mV to −300 mV and back to 0 mV, while measuring the resultant current. Accordingly, chart 800 depicts the current along the vertical axis at corresponding potentials between 0 mV and −300 mV, along the horizontal axis. Data graph 802 represent a signal measured at an electrode, such as working electrode 702 of FIG. 7, in the absence of a target marker. Data graph 704 represents a signal measured at an electrode, such as working electrode 702 of FIG. 7, in the presence of a target marker. As can be seen on data graph 804, the signal recorded in the presence of the target molecule provides a higher amplitude current signal, particularly when comparing peak 808 with peak 806 located at approximately −100 mV. Accordingly, the presence and absence of the marker can be differentiated.

In certain applications, a single electrode or sensor is configured with two or more probes, arranged next to each other, or on top of or in close proximity within the chamber so as to provide target and control marker detection in an even smaller point-of-care size configuration. For example, a single electrode sensor may be coupled to two types of probes, which are configured to hybridize with two different markers. In certain approaches, a single probe is configured to hybridize and detect two markers. In certain approaches, two types of probes may be coupled to an electrode in different ratios. For example, a first probe may be present on the electrode sensor at a ratio of 2:1 to the second probe. Accordingly, the sensor is capable of providing discrete detection of multiple analytes. For example, if the first marker is present, a first discrete signal (e.g., current) magnitude would be generated, if the second marker is present, a second discrete signal magnitude would be generated, if both the first and second marker are present, a third discrete signal magnitude would be generated, and if neither marker is present, a fourth discrete signal magnitude would be generated. Similarly, additional probes could also be implemented for increased numbers of multi-target detection.

FIG. 9 depicts a detection system using a nanostructured microelectrode for electrochemical detection of a nucleotide strand, in accordance with an implementation. Nanostructured microelectrodes are microscale electrodes with nanoscale features. Nanostructured microelectrode systems are described in further detail in U.S. application Ser. No. 13/061,465, U.S. Pat. Nos. 7,361,470 and 7,741,033, and PCT Application No. PCT/US12/02401.5, which are hereby incorporated by reference herein in their entireties. Functionalized detection unit 900 utilizes a nanostructured microelectrode as a working electrode, which increases the sensitivity of the system by dramatically increasing the surface-area of the working electrode. Probe 318 is tethered to working electrode 306 along with other probes that are chemically identical to probe 318, using any suitable method described herein. Probe 318 is specific to target marker 320, and may be any suitable type of probe, such as a PNA probe. Probe 318 may be tethered to working electrode 306 using any suitable method. For example, nitrogen containing nanostructured microelectrodes (e.g., TiN, WN, or TaN) can bind with an amine functional group of probe 318. Upon introduction target marker 320 into the sample well, complex 322 may be formed by selective binding get marker 320 with probe 318. Electrochemical reagents may be pre-mixed with the sample upon application to the sample well, in some implementations, the sample is flushed from the sample wells after a time interval has passed to allow binding of target marker 320 with probe 318, and a solution containing electrochemical reagents is then added to the sample well to enable electrochemical detection.

FIG. 10 shows an exemplary system for detecting a target marker in accordance with the various implementations described herein. The detection system 1000 includes solid support 1002, lead 1004, aperture layer 1006, counter electrode 1008, reference electrode 1010, and working electrode 1012, which extends from lead 1002 through aperture 1016. However, any suitable configuration of electrodes may be used. If the sample contains a target marker of interest, complex 1014 may form on the surface of working electrode 1012.

The detection system 1000 shown in FIG. 10 incorporates an illustrative three-electrode potentiostat configuration, however it should be understood that any suitable configuration of components may be used. Lead 1004 is connected to the output terminal of control amplifier 1018. Counter electrode 1008 is connected to resistor 1020, which is grounded. It should be understood, however, that resistor 1020 does not necessarily need to be grounded. For example, counter electrode 1008 can be held at the same substantially fixed potential as the remaining leads described in reference to FIGS. 1, 2A, 2B, and 5, so as to reduce current flow from those leads to counter electrode 1008 while a measurement is performed. Detection module 1022 is connected across resistor 1020, which is operable to determine a current through resistor 1020 based on a measured potential and the value of resistance. The detection module 1022 may be configured to provide real-time current measurement in response to any input waveform. Reference electrode 100 is connected to the inverting terminal of control amplifier 1018. Signal generator 1024 is connected to the non-inverting terminal of control amplifier 1018. This configuration maintains constant potential at the working electrode while allowing for accurate measurements of the current.

Control and communication unit 1026 is operably coupled to detection module 1022 and signal generator 1024. Control and communication unit 1026 may synchronize the input waveforms and output measurements, and may receive and store the input and output in a memory. In some implementations, control and communication unit 1026 is a separate unit that interfaces with detection system 400. For example, detection system 1000 may be a disposable cartridge with a plurality of input and output terminals that can interface with control and communication unit 1026. In some implementations, control and communication unit 1026 is operably coupled to a display unit that displays the output as a function of input. In some implementations, control and communication unit 1026 transmits the input and output information to a remote destination for storage and display. For example, control and communication unit 1026 could be a mobile device or capable of being interfaced with a mobile device. In some implementations, control and communication unit 1026 provides power to the detection system 1000. Detection system 1000 may be powered using any suitable power source, including a battery or a plugged-in AC power source.

Figure 11A:
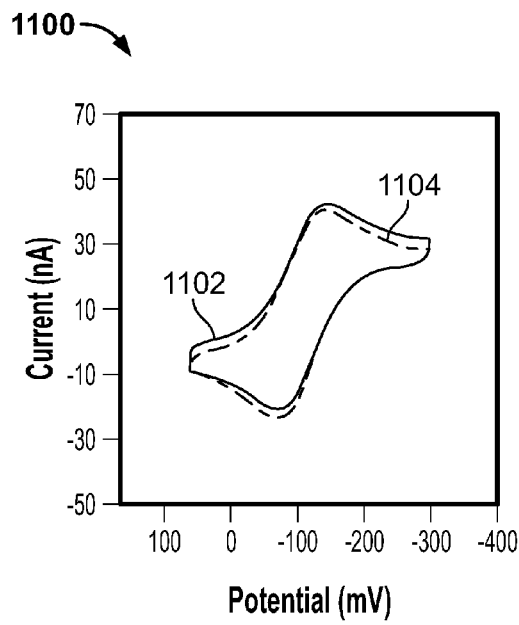
FIGS. 11A-11C show response signal measurements demonstrating the electrical isolation of the sample wells, according to an implementation.
Figure 11B:
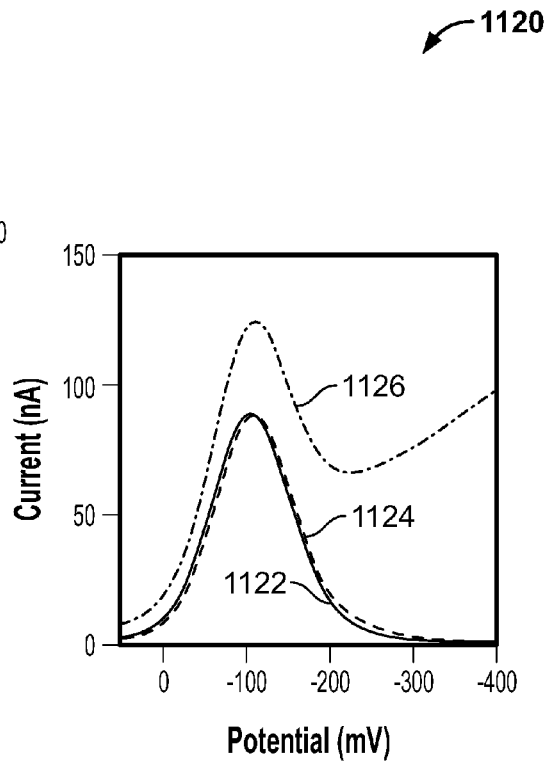
Figure 11C:
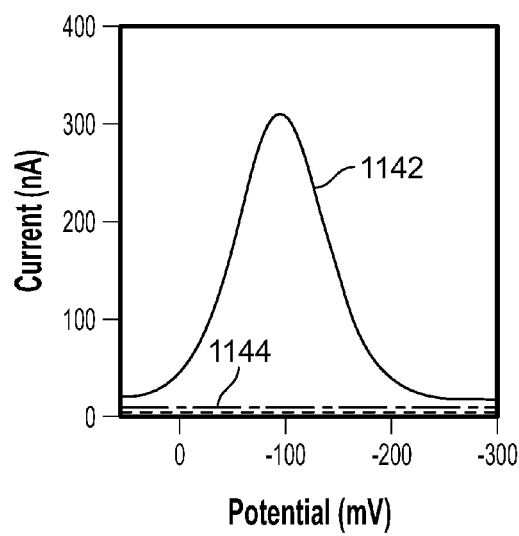

FIG. 11 shows response signal measurements demonstrating the electrical isolation of the sample wells. In the example of FIG. 7, inactive working electrodes that are electrically coupled to the active working electrodes were held at close to the ground potential during measurements. However, as discussed herein, the inactive working electrodes can be held at any suitable substantially fixed potential that reduces electrical cross-talk between the inactive electrodes and the counter electrode being used for the measurements. Cyclic voltammetry of ferrocyanide was used to evaluate electrochemical characteristics of an electrochemical chip versus a serially-connected chip. From chart 1100, it can be seen that the chip signal 1102 was nearly identical the serially-connected chip signal 1104. Chart 1120 shows differential pulse voltammetry scans of ferrocyanide that compare the effects of grounding the inactive working electrodes. The grounded sensor signal 1122 is nearly identical to an individual, non-multiplexed sensor signal 1124. By contrast, the ungrounded signal 1126 in the chart 1120 illustrates results of measurements performed without holding the inactive electrodes at a substantially fixed potential. As shown by chart 1120, not holding the inactive signal at a substantially fixed potential leads to a significant level of cross-talk that distorts the response signal and reduces the sensitivity of the measurements. Chart 1140 compares a selected sample well signal 1142 with an adjacent sample well signal 1144. The selected sample well was filled with 2 mM $Fe(CN)_6^{3-}$, and the adjacent sample well was filled with 0.1× PBS buffer. The results indicate that there is minimal perturbation of the adjacent sample well when the electrochemical reagent is added to the selected sample well.

Figure 12C:
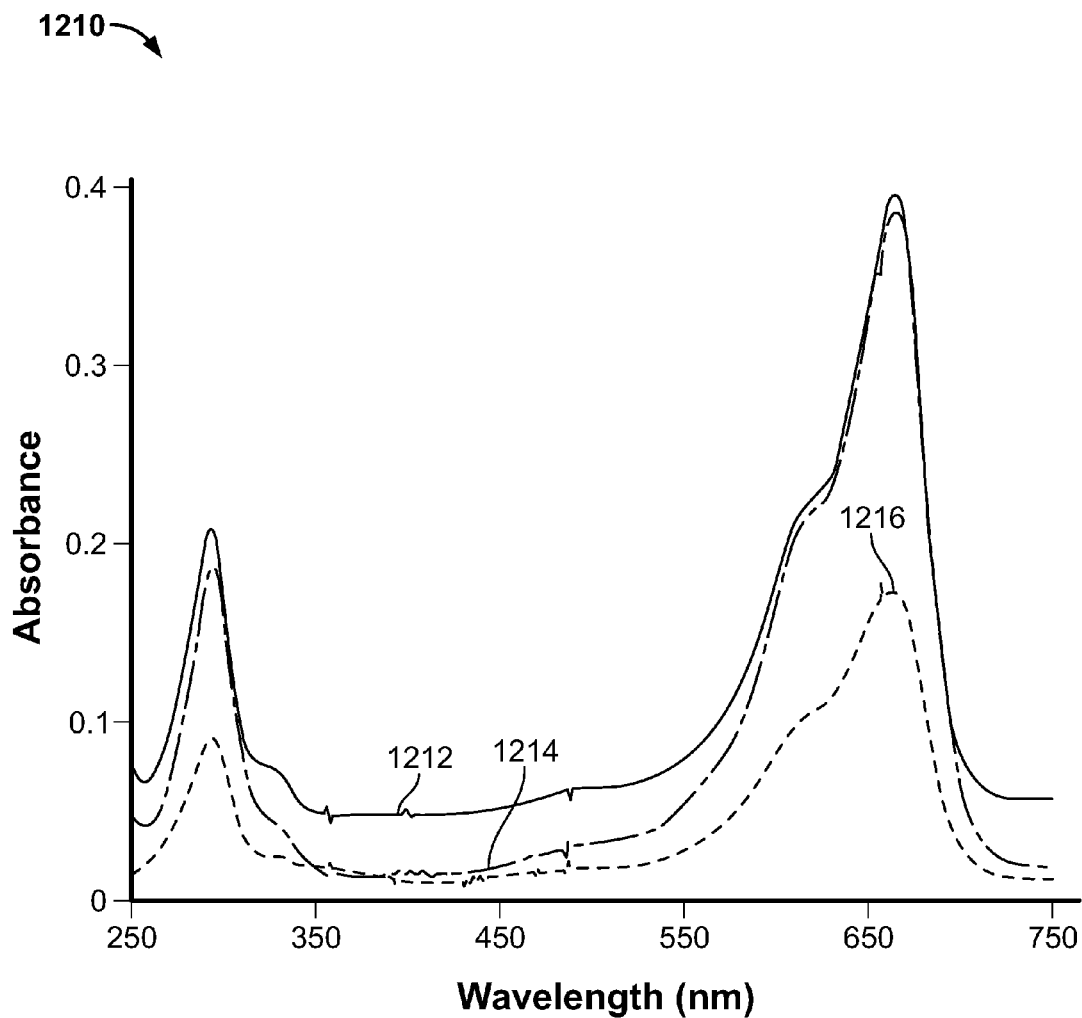

FIG. 12 shows an experimental setup that demonstrates the electrical isolation of the sample wells. Methylene blue (MB) is a chemical that can be electrochemically reduced to a colorless form. MB (100 µM MB and 50 mM NaCl) was loaded into all sample wells as shown in setup 1202, and working electrodes within the middle sample well of the chip were held at a reduction potential of −650 mV for 1 hour. The reduction of MB was observed visually, as shown in setup 1204, in the sample well under bias, providing a qualitative measure of electrical isolation. Chart 1210 shows absorbance spectra as measured with a UV-vis spectrophotometer. Measurements of the absorbance of a control well 1212, an adjacent well 1214, and an activated well 1216 (corresponding to the middle sample well) confirmed that the significant loss in MB absorbance is detected in the middle sample well.

Figure 13A:
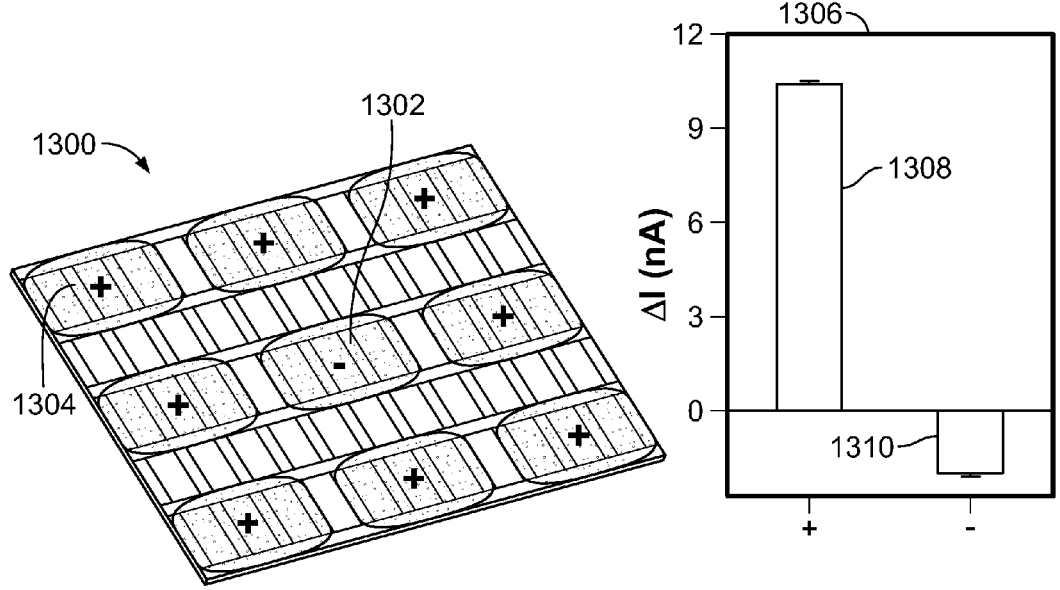
FIGS. 13A-13B show an experimental setup demonstrating the presence or absence of a sample, according to an implementation.
Figure 13B:
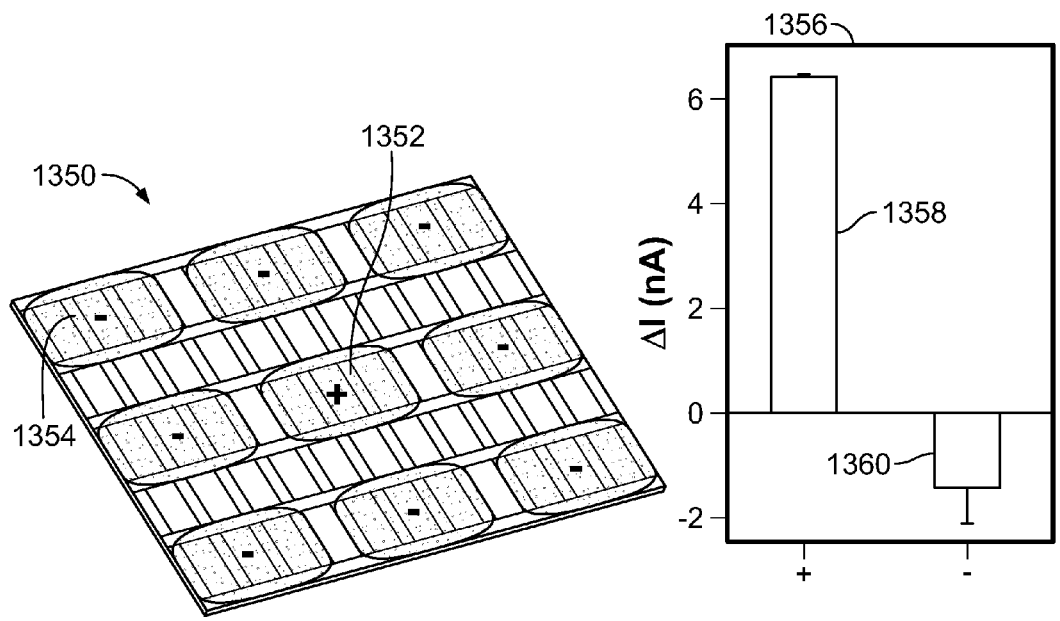

FIG. 13 shows an experimental setup demonstrating the presence or absence of a target marker in a sample. Groups of sensor units were functionalized with target-specific PNA probes. Sample well was filled with 1.5 µL of complementary or non-complementary probe solution initially heated to 60° C. for 5 min, containing 100 nM probe and 900 nM mercaptohexanol, and incubated directly on the chip for 30 min at room temperature. Chips were washed with 0.1×PBS 2× for 5 minutes after probe deposition and an initial DPV background scan in electrochemical solution (10 µM $Ru(NH_3)_6^{3+}$ and 4 mM $Fe(CN)_6^{3-}$ in 0.1×PBS buffer) was performed. Chips were then hybridized with 10 nM complementary target in 1×PBS buffer for 30 min at 37° C. Chips were washed with 0.1×PBS buffer twice for 5 min after target hybridization and differential pulse voltammetry scans in electrochemical solution were performed.

Sensor system 1300 was designed such that the sensors of a non-binding region 1302 was functionalized with a PNA probe sequence that would not bind a specific target DNA sequence, and was surrounded by binding regions 1304 that had sensors functionalized with a PNA probe that would bind the DNA target. As observed in chart 1306, a large positive response signal 1308 was obtained from the sensors of binding regions 1304, while a small negative response signal 1310 change was observed from the sensors of non-binding, region 1302. These results indicate that with the nanoamp levels of current generated during sequence analysis, crosstalk between sensors does not influence the results obtained. Similar results were observed for sensor system 1350, which included binding region 1352 and non-binding regions 1354.

Figure 14A:
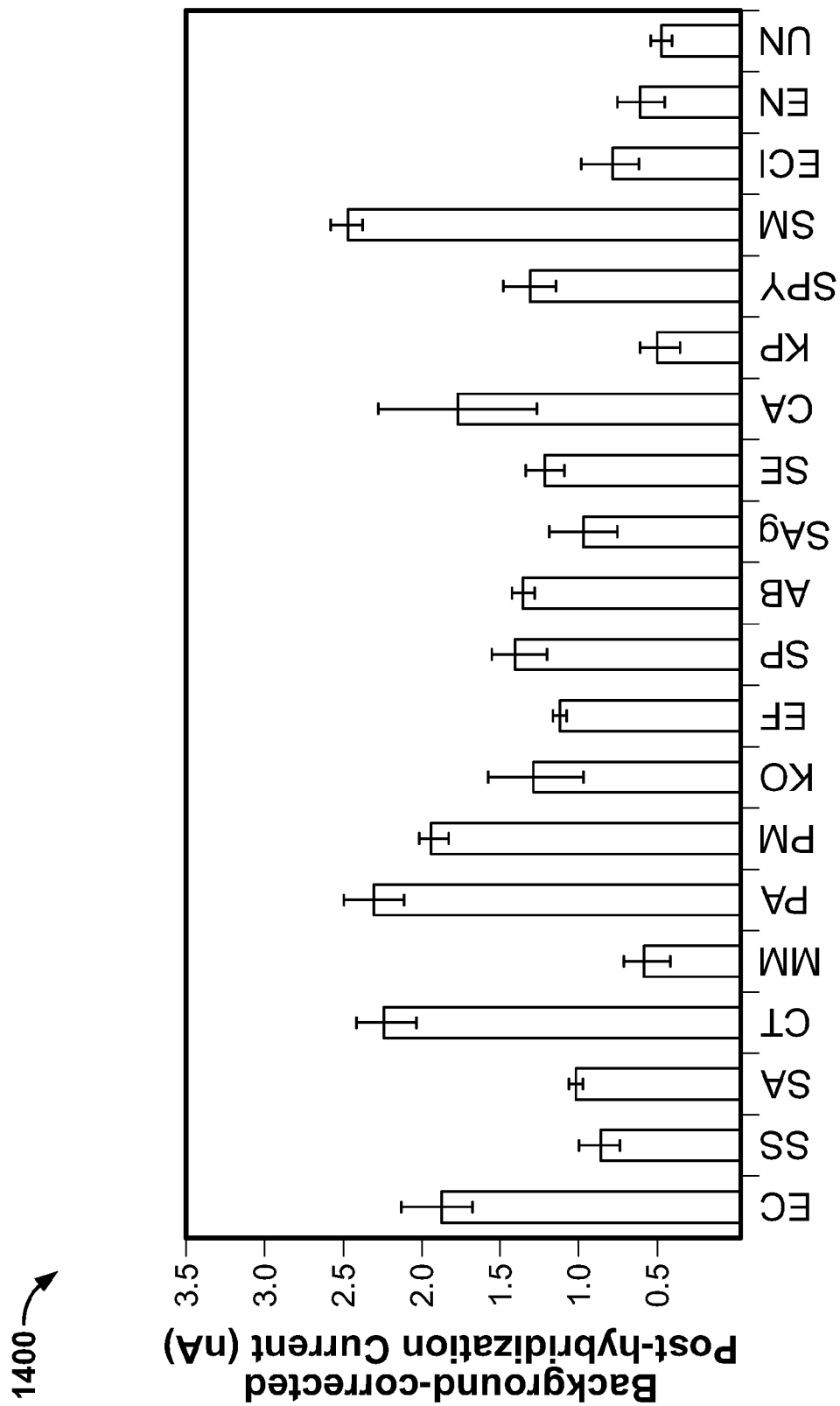
FIGS. 14A-14C show sensitivity and specificity test results for detecting various targets, according to some implementations.
Figure 14B:
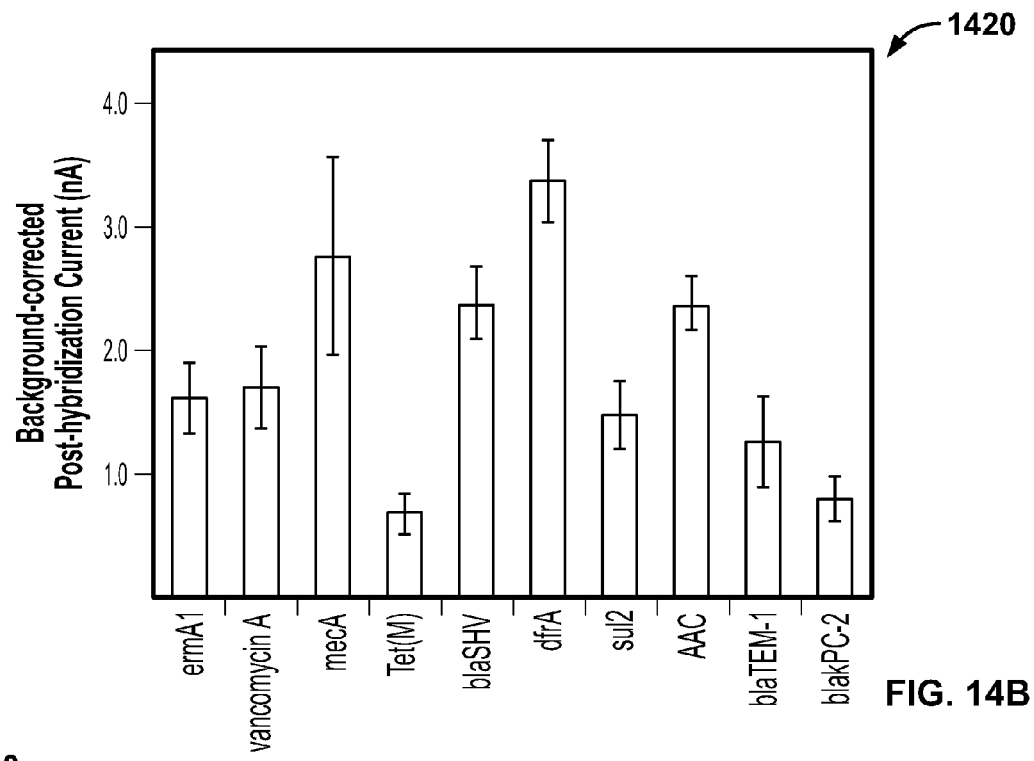
Figure 14C:
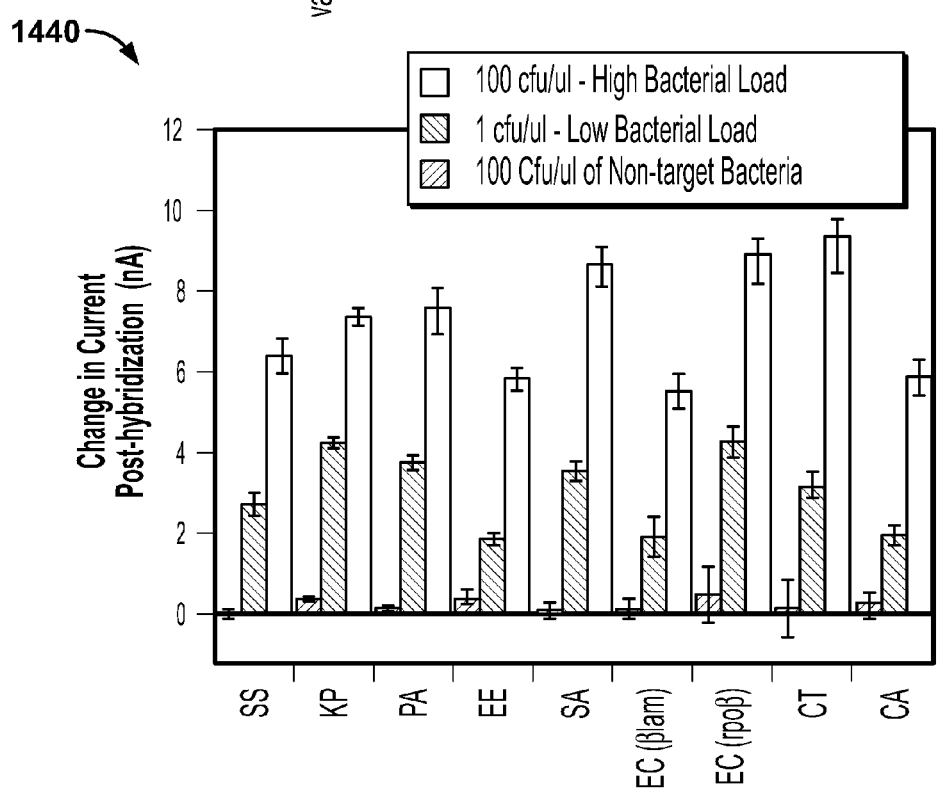

FIG. 14 shows data related to sensitivity and specificity for detecting various targets. A set of PNA probes were designed, synthesized, tested, and validated for sensitivity and specificity. The following pathogen probe sequences ($NH_2$-Cys-Gly-Asp SEQUENCE Asp-$CONH_2$) that are specific to mRNA targets were synthesized using a Protein Technologies Prelude peptide synthesizer: (*E. coli*=EC) ATC-TGC-TCT-GTG-GTG-TAG-TT (SEQ ID NO:1), (*P. mirabilis*=PM) AAG-CGA- GCT-AAC-ACA-TCT-AA (SEQ ID NO:2), (*S. saprophyticus*=SS) AAG-TAA-GAC-ATT-GAT- GCA-AT (SEQ ID NO:3), (*S. aureus*=SA) CCA-CAC-ATC-TTA-TCA-CCA-AC (SEQ ID NO:4, (*K. pneumonia*=KP) GTT-TAG-CCA-CGG-CAG-TAA-CA (SEQ ID NO:5), (*M. morganii*=MM) CGC-TTT-GGT-CCG-AAG-ACA-TTA-T (SEQ ID NO:6), (*P. aeruginosa*=PA) CCC- GGG-GAT-TTC-ACA-TCC-AAC-TT (SEQ ID NO:7), (*K. oxytoca*=KO) CCA-GTA-GAT-TCG- TCA-ACA-TA (SEQ ID NO:8), (*S. marescens*=SM) TGC-GAG-TAA-CGT-CAA-TTG-ATG-A (SEQ ID NO:9), (E. faecalis =EF) CGA-CAC-CCG-AAA-GCG-CCT-TT (SEQ ID NO:10), (*A. Baumannii*=AB) CGT-CAA-GTC-AGC-ACG-TAA-TG (SEQ ID NO:11), (*S. pyogenes*=SPy) TCT-TGA-CGA-CGG-ATT-TCC-AC (SEQ ID NO:12), (*S. agalactiae* =SAg) GTT-CAG-TAA- CTA-CAG-CAT-AA (SEQ ID NO:13), (*S. epidermidis* =SE) AAA-TAA-CTC-ATT-GAG-GCA- AC (SEQ ID NO:14), (*E. cloacae*=ECl) TCA-ACG-TAA-TCT-TTC-GCG-GC (SEQ ID NO:15), (*S. pneumonia*=SP) GTT-ACG-ACG-CGA-TCT-GGA-TC (SEQ ID NO:16), (*C. albicans*=CA) GCT-ATA-ACA-CAC-AGC-AGA-AG (SEQ ID NO:17), (*C. trachomatis*=CT) TGC-ATT-TGC- CGT-CAA-CTG (SEQ ID NO:18), (*enterobacter* genus =EN) ACT-TTA-TGA-GGT-CCG-CTT- GCT-CT (SEQ ID NO:19), (Universal bacteria probe =UB) GGT-TAC-CTT-GTT-ACG-ACT-T (SEQ ID NO:20).

Multiplexed chips were used in the assessment of 30 probes for pathogens and antibiotic resistance markers, as shown by charts 1400 and 1420. The pathogen probes were targeted against either the RNA polymerase β mRNA (rpo β, or a ribosomal RNA, and the antibiotic resistance probes were targeted against known sequences correlated with drug deactivation. To screen sequences for specificity, the response obtained when a solution containing a 1 nM concentration of a complementary target was compared to a solution containing a 100 nM concentration of a non-complementary target. The background-subtracted current generated was then analyzed, and for the large majority of the probes that were tested, the current obtained was greater than the baseline by three standard deviations, indicating high levels of specificity. The sensitivity of sensors modified with these probes was then tested against a panel of pathogens amenable to culture, as shown by chart 1440. Unpurified bacterial lysates containing 1 cfu/µL and 100 cfu/µL were incubated with the sensors, and electrochemical signals compared to those obtained when the same sensor type was exposed to 100 cfu/µL of non-target bacteria (*E. coli* for each trial except for those testing the sensitivity of the *E. coli* probes, where *S. saprophyticus* was used). In each case, high sensitivity and specificity were achieved, indicating that this system is capable of clinically-relevant detection.

Figure 15D:
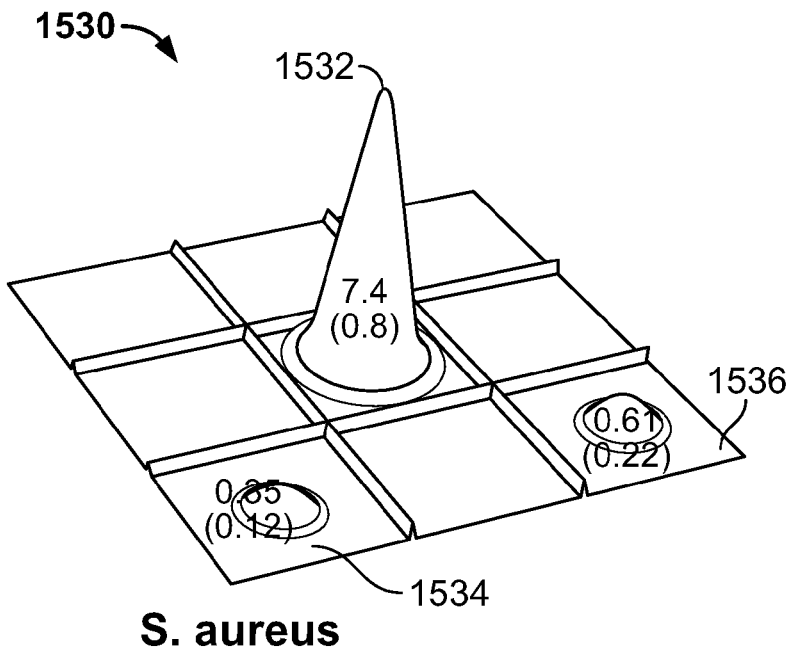
Figure 15E:
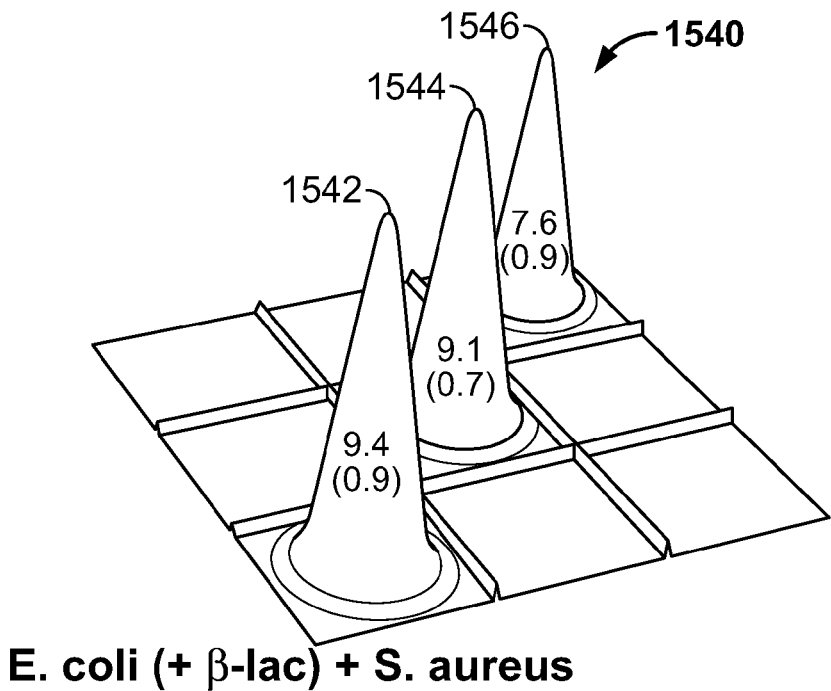

FIG. 15 shows the multiplexed detection of multiple targets using clinically-relevant target concentrations. Electrochemical chip 1500 was functionalized simultaneously with 9 probes by placing solution droplets containing the specific probes at 9 locations on the chip 1500. The chip 1500 was then challenged with bacterial lysates at 100 cfu/µL. Chip 1500 was first challenged with *E. coli* lysate, which was obtained using a Claremont BioSolutions OmniLyse rapid cell lysis kit. For each of plots 1510, 1520, 1530, 1540, the regions correspond to the sample locations on chip 1500, and the peaks are representative of output current averaged over multiple working electrodes that correspond to a particular probe. The numbers that accompany each peak correspond to an average current, and the numbers in parentheses correspond to a standard deviation.

As shown in plot 1510, the response 1512 of sensors modified with the *E. coli* probe (EC) targeted against the RNA polymerase gene (rpo β) was significant, while no other probe responses, for example response 1514, were significant. Chip 1500 was further challenged with a form of antibiotic resistant *E. coli* that contains a β-lactamase gene. As shown in plot 1520, EC response 1522 and β-lac response 1524 were significant, while no other probe responses, for example response 1526, were significant. This result indicates that chip 1500 is capable of classifying pathogens and detecting antibiotic resistance simultaneously. Chip 1500 was further challenged with lysates of *S. aureus* (SA) to confirm successful detection of gram-positive pathogens. Only working electrodes functionalized with SA probe showed a significant electrochemical response 1532, while no other probe responses, for example signal 1534 and 1536, were significant. Chip 1500 was further challenged with a mixture of *S. aureus* (SA) and antibiotic resistant *E. coli* (+β-lac) to evaluate the performance of chips brought into contact with several analytes producing a positive response. As shown in plot 1540, only working electrodes functionalized with EC, SA and β-lac probes exhibited significant electrochemical responses 1542, 1544, 1546 to the mixed sample. These results illustrate that the multiplexing provided by the illustrative electrochemical chips described herein enable the parallel detection of multiple analytes at clinically relevant levels.

The foregoing is merely illustrative of the principles of the disclosure, and the systems, devices, and methods can be practiced by other than the described implementations, which are presented for the purposes of illustration and not of limitation. It is to be understood that the systems, devices, and methods disclosed herein, while shown for use in the multiplexed detection of disease and pathogens, may be applied to systems, devices, and methods to be used in other applications that require multiplexed read-out channels and on-chip detection of chemical and biochemical reactions.

Variations and modifications will occur to those of skill in the art after reviewing this disclosure. The disclosed features may be implemented, in any combination and subcombination (including multiple dependent combinations and subcombinations), with one or more other features described herein. The various features described or illustrated above, including any components thereof, may be combined or integrated in other systems. Moreover, certain features may be omitted or not implemented.

Examples of changes, substitutions, and alterations are ascertainable by one skilled in the art and could be made without departing from the scope of the information disclosed herein. All references cited are hereby incorporated by reference herein in their entireties and made part of this application.

What is claimed is:

1. A multiplexed electrochemical detection system, comprising:
   a solid support;
   a plurality of leads affixed to the solid support, each of the plurality of leads extending in a first direction in the solid support and being adapted to be electrically coupled to a first plurality of working electrodes, wherein each of the first plurality of working electrodes is housed in a different one of a plurality of sample wells within the solid support;
   a first counter electrode extending in a second direction different from the first direction and adapted to be electrically coupled to a second plurality of working electrodes, wherein the second plurality of working electrodes includes at least one of the first plurality of working electrodes, and wherein each of the second plurality of working electrodes is housed in a first sample well in the plurality of sample wells;
   a first signal input interface adapted to be electrically coupled to a first lead of the plurality of leads and adapted to selectively apply a first signal to the first lead;
   a second signal input interface adapted to be electrically coupled to a first subset of the plurality of leads and adapted to selectively apply a substantially fixed potential to each of the first subset of the plurality of leads; and
   a detection circuitry configured to:
      measure a first response signal from the first counter electrode while the second signal input interface applies the substantially fixed potential to the remainder of the second plurality of leads.

2. The system of claim 1, further comprising:
   a second counter electrode adapted to be electrically coupled to a third plurality of working electrodes including at least one of the first plurality of working electrodes, wherein:
   the first signal input interface is adapted to be electrically coupled to a second lead of the plurality of leads and adapted to selectively apply a third signal to the second lead;
   the second signal input interface adapted to be electrically coupled to a second subset of the plurality of leads and adapted to selectively apply a substantially fixed potential to each of the second subset of the plurality of leads, and
   the detection circuitry is further configured to:
      measure a second response signal from the second counter electrode while while the second signal input interface applies the substantially fixed potential.

3. The system of claim 2, wherein the second plurality of working electrodes are adapted to be electrically coupled to the first counter electrode by the presence of a first fluid portion of the sample capable of simultaneously contacting each of the second plurality of working electrodes and the first counter electrode.

4. The system of claim 3, wherein the third plurality of working electrodes are adapted to be electrically coupled to the second counter electrode by the presence of a second fluid portion of the sample capable of simultaneously contacting each of the third plurality of working electrodes and the second counter electrode, wherein the second fluid portion is substantially physically isolated from the first fluid portion during said measuring of the first and second response signals.

5. The system of claim 4, wherein each of the plurality of leads is arranged in one of a plurality of rows on the solid support, and each of the first and second sample wells is formed from first and second elongated channels, respectively, that run perpendicular to each of the plurality of rows.

6. The system of claim 5, wherein each of the first and second channels comprise hydrophobic and hydrophilic regions.

7. The system of claim 6, further comprising a first plurality of probes tethered to at least some of the second plurality of working electrodes, wherein the first plurality of probes is selected to hybridize with a first target analyte.

8. The system of claim 7, further comprising a second plurality of probes tethered to at least some of the third plurality of working electrodes, wherein the second plurality of probes is selected to hybridize with a second target analyte but not the first target analyte.

9. The system of claim 8, wherein each of the first and second counter electrodes are adapted to couple to a common potentiostat, and wherein the detection circuitry is further configured to measure the first and second response signals sequentially using the common potentiostat.

10. The system of claim 8, wherein the first counter electrode is adapted to couple to a first potentiostat and second counter electrode is adapted to couple to a second potentiostat, and wherein the detection circuitry is further configured to measure the first and second response signals sequentially using the first and second potentiostats, respectively.

11. The system of claim 8, wherein the first and second pluralities of working electrodes comprise one or more nanostructured microelectrodes.

12. The system of claim 11, further comprising applying to the electrochemical detector an electrochemical reagent comprising $Ru(NH3)_6^{3+}$ and $Fe(CN)_6^{3-}$.

13. The system of claim 12, wherein the first and second pluralities of probes are selected from the group consisting of nucleic acids, peptide nucleic acids, locked nucleic acids, proteins, and peptides.

14. The system of claim 13, wherein the detection circuitry is configured to interface with a processor, the processor being configured to determine that a magnitude of the first response signal is greater than a threshold value.

15. The system of claim 14, wherein the processor is further configured to provide an indicator of whether the first target analyte is present in the sample, the indicator selected from the group consisting of amplitude magnitude of the first response signal, a concentration of the first target analyte determined based on the first response signal, a color-coded indicator selected based on the first response signal, a symbol selected based on the first response signal, a graphical representation of the first response signal over a plurality of values of the first voltage signal, and any suitable combination thereof.

16. The system of claim 15, further comprising a plurality of reference electrodes, each adapted to be electrically coupled to one of the plurality of sample wells, the plurality of reference electrodes including a first reference electrode adapted to be coupled to the first sample well.

17. The system of claim 16, wherein the first reference electrode is paired with the first counter electrode.

18. The system of claim 17, wherein the sample is a liquid sample.

19. The system of claim 18, wherein the sample contains bacteria.

20. The system of claim 19, further comprising a lysing channel that lyses the bacteria in the sample prior to introducing the sample into the multiplexed electrochemical detector.

21. The system of claim 1, wherein the substantially fixed potential is selected to reduce current flow from the first subset of the plurality of leads to the first counter electrode.

22. The system of claim 1, wherein the substantially fixed potential corresponds to a ground potential.

* * * * *

SEQUENCE LISTING

```
<160> NUMBER OF SEQ ID NOS: 20

<210> SEQ ID NO 1
<211> LENGTH: 20
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 1
atctgctctg tggtgtagtt                                             20

<210> SEQ ID NO 2
<211> LENGTH: 20
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 2
aagcgagcta acacatctaa                                             20

<210> SEQ ID NO 3
<211> LENGTH: 20
```

```
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 3
aagtaagaca ttgatgcaat                                               20

<210> SEQ ID NO 4
<211> LENGTH: 20
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 4
ccacacatct tatcaccaac                                               20

<210> SEQ ID NO 5
<211> LENGTH: 20
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 5
gtttagccac ggcagtaaca                                               20

<210> SEQ ID NO 6
<211> LENGTH: 22
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 6
cgctttggtc cgaagacatt at                                            22

<210> SEQ ID NO 7
<211> LENGTH: 23
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 7
cccggggatt tcacatccaa ctt                                           23

<210> SEQ ID NO 8
<211> LENGTH: 20
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 8
ccagtagatt cgtcaacata                                               20

<210> SEQ ID NO 9
<211> LENGTH: 22
<212> TYPE: DNA
```

```
<213> ORGANISM: Artificial Sequence
<220> FEATURE:
<223> OTHER INFORMATION: Description of Artificial Sequence: Synthetic
      probe

<400> SEQUENCE: 9
tgcgagtaac gtcaattgat ga                                              22

<210> SEQ ID NO 10
<211> LENGTH: 20
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 10
cgacacccga aagcgccttt                                                 20

<210> SEQ ID NO 11
<211> LENGTH: 20
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 11
cgtcaagtca gcacgtaatg                                                 20

<210> SEQ ID NO 12
<211> LENGTH: 20
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 12
tcttgacgac ggatttccac                                                 20

<210> SEQ ID NO 13
<211> LENGTH: 20
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 13
gttcagtaac tacagcataa                                                 20

<210> SEQ ID NO 14
<211> LENGTH: 20
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 14
aaataactca ttgaggcaac                                                 20

<210> SEQ ID NO 15
<211> LENGTH: 20
<212> TYPE: DNA
<213> ORGANISM: Artificial Sequence
```

-continued

```
<220> FEATURE:
<223> OTHER INFORMATION: Description of Artificial Sequence: Synthetic
      probe

<400> SEQUENCE: 15
tcaacgtaat ctttcgcggc                                                    20

<210> SEQ ID NO 16
<211> LENGTH: 20
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 16
gttacgacgc gatctggatc                                                    20

<210> SEQ ID NO 17
<211> LENGTH: 20
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 17
gctataacac acagcagaag                                                    20

<210> SEQ ID NO 18
<211> LENGTH: 18
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 18
tgcatttgcc gtcaactg                                                      18

<210> SEQ ID NO 19
<211> LENGTH: 23
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 19
actttatgag gtccgcttgc tct                                                23

<210> SEQ ID NO 20
<211> LENGTH: 19
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 20
ggttaccttg ttacgactt                                                     19
```